United States Patent
el Kaliouby et al.

(10) Patent No.: US 10,482,333 B1
(45) Date of Patent: *Nov. 19, 2019

(54) MENTAL STATE ANALYSIS USING BLINK RATE WITHIN VEHICLES

(71) Applicant: Affectiva, Inc., Boston, MA (US)

(72) Inventors: Rana el Kaliouby, Milton, MA (US); Abdelrahman N. Mahmoud, Somerville, MA (US); Seyedmohammad Mavadati, Watertown, MA (US); Panu James Turcot, Pacifica, CA (US)

(73) Assignee: Affectiva, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/126,615

(22) Filed: Sep. 10, 2018

Related U.S. Application Data

(63) Continuation-in-part of application No. 15/670,791, filed on Aug. 7, 2017, now Pat. No. 10,074,024, (Continued)

(51) Int. Cl.
*B60Q 1/00* (2006.01)
*G06K 9/00* (2006.01)
(Continued)

(52) U.S. Cl.
CPC ........ *G06K 9/00845* (2013.01); *A61B 5/0077* (2013.01); *A61B 5/1103* (2013.01);
(Continued)

(58) Field of Classification Search
CPC ........... G06K 9/00845; G06K 9/00281; G16H 50/20; A61B 5/0077; A61B 5/1103;
(Continued)

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Zhen Y Wu
(74) *Attorney, Agent, or Firm* — Adams Intellex, PLC

(57) ABSTRACT

Mental state analysis is performed using blink rate within vehicles. Video is obtained of an individual or a group within a vehicle. The video is analyzed to detect a blink event based on a classifier, where the blink event is determined by identifying that eyes are closed for a frame in the video. A blink duration is evaluated for the blink event. Blink-rate information is determined using the blink event and one or more other blink events. The evaluating can include evaluating blinking for a group of people. The blink-rate information is compensated using the processors for a context. Mental states of the individual are inferred for the blink event, where the mental states are based on the blink event, the blink duration of the individual, and the blink-rate information that was compensated. A difference in blinking between the individual and the remainder of a group can be determined.

28 Claims, 20 Drawing Sheets

Related U.S. Application Data which is a continuation-in-part of application No. 15/666,048, filed on Aug. 1, 2017.

(60) Provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/442,291, filed on Jan. 4, 2017, provisional application No. 62/442,325, filed on Jan. 4, 2017.

(51) Int. Cl.
*A61B 5/16* (2006.01)
*B60K 28/06* (2006.01)
*B60R 11/04* (2006.01)
*A61B 5/00* (2006.01)
*A61B 5/11* (2006.01)
*A61B 5/18* (2006.01)
*A61B 5/0205* (2006.01)
*G06Q 30/02* (2012.01)
*G16H 50/20* (2018.01)

(52) U.S. Cl.
CPC ............. *A61B 5/165* (2013.01); *A61B 5/18* (2013.01); *A61B 5/6893* (2013.01); *B60K 28/06* (2013.01); *B60R 11/04* (2013.01); *G06K 9/00281* (2013.01); *A61B 5/02055* (2013.01); *G06Q 30/0271* (2013.01); *G06T 2207/30201* (2013.01); *G06T 2207/30268* (2013.01); *G16H 50/20* (2018.01)

(58) Field of Classification Search
CPC ......... A61B 5/165; A61B 5/18; A61B 5/6893; A61B 5/02055; B60K 28/06; B60R 11/04; G06F 19/00; G06Q 30/0271; G06T 2207/30201; G06T 2207/30268
USPC ........................................................ 340/439
See application file for complete search history.

(56) References Cited

U.S. PATENT DOCUMENTS

| | | | |
|---|---|---|---|
| 3,870,034 A | 3/1975 | James | |
| 4,353,375 A | 10/1982 | Colburn et al. | |
| 4,448,203 A | 5/1984 | Williamson et al. | |
| 4,794,533 A | 12/1988 | Cohen | |
| 4,807,642 A | 2/1989 | Brown | |
| 4,817,628 A | 4/1989 | Zealear et al. | |
| 4,950,069 A | 8/1990 | Hutchinson | |
| 4,964,411 A | 10/1990 | Johnson et al. | |
| 5,016,282 A | 5/1991 | Tomono et al. | |
| 5,031,228 A | 7/1991 | Lu | |
| 5,219,322 A | 6/1993 | Weathers | |
| 5,247,938 A | 9/1993 | Silverstein et al. | |
| 5,259,390 A | 11/1993 | Maclean | |
| 5,507,291 A | 4/1996 | Stirbl et al. | |
| 5,572,596 A | 11/1996 | Wildes et al. | |
| 5,619,571 A | 4/1997 | Sandstorm et al. | |
| 5,647,834 A | 7/1997 | Ron | |
| 5,649,061 A | 7/1997 | Smyth | |
| 5,663,900 A | 9/1997 | Bhandari et al. | |
| 5,666,215 A | 9/1997 | Fredlund et al. | |
| 5,725,472 A | 3/1998 | Weathers | |
| 5,741,217 A | 4/1998 | Gero | |
| 5,760,917 A | 6/1998 | Sheridan | |
| 5,762,611 A | 6/1998 | Lewis et al. | |
| 5,772,508 A | 6/1998 | Sugita et al. | |
| 5,772,591 A | 6/1998 | Cram | |
| 5,774,591 A | 6/1998 | Black et al. | |
| 5,802,220 A | 9/1998 | Black et al. | |
| 5,825,355 A | 10/1998 | Palmer et al. | |
| 5,886,683 A | 3/1999 | Tognazzini et al. | |
| 5,898,423 A | 4/1999 | Tognazzini et al. | |
| 5,920,477 A | 7/1999 | Hoffberg et al. | |
| 5,945,988 A | 8/1999 | Williams et al. | |
| 5,959,621 A | 9/1999 | Nawaz et al. | |
| 5,969,755 A | 10/1999 | Courtney | |
| 5,983,129 A | 11/1999 | Cowan et al. | |
| 5,987,415 A | 11/1999 | Breese et al. | |
| 6,004,061 A | 12/1999 | Manico et al. | |
| 6,004,312 A | 12/1999 | Finneran et al. | |
| 6,008,817 A | 12/1999 | Gilmore, Jr. | |
| 6,026,321 A | 2/2000 | Miyata et al. | |
| 6,026,322 A | 2/2000 | Korenman et al. | |
| 6,056,781 A | 5/2000 | Wassick et al. | |
| 6,067,565 A | 5/2000 | Horvitz | |
| 6,088,040 A | 7/2000 | Oda et al. | |
| 6,091,334 A * | 7/2000 | Galiana ................. G08B 21/06 | 340/439 |
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ball et al. | |
| 6,222,607 B1 | 4/2001 | Szajewski et al. | |
| 6,309,342 B1 | 10/2001 | Blazey et al. | |
| 6,327,580 B1 | 12/2001 | Pierce et al. | |
| 6,349,290 B1 | 2/2002 | Horowitz et al. | |
| 6,351,273 B1 | 2/2002 | Lemelson et al. | |
| 6,437,758 B1 | 8/2002 | Nielsen et al. | |
| 6,443,840 B2 | 9/2002 | Von Kohorn | |
| 6,530,082 B1 | 3/2003 | Del Sesto et al. | |
| 6,577,329 B1 | 6/2003 | Flickner et al. | |
| 6,606,102 B1 | 8/2003 | Odom | |
| 6,629,104 B1 | 9/2003 | Parulski et al. | |
| 6,724,920 B1 | 4/2004 | Berenz et al. | |
| 6,792,458 B1 | 9/2004 | Muret et al. | |
| 6,847,376 B2 | 1/2005 | Engeldrum et al. | |
| 7,003,135 B2 | 2/2006 | Hsieh et al. | |
| 7,013,478 B1 | 3/2006 | Hendricks et al. | |
| 7,027,621 B1 | 4/2006 | Prokoski | |
| 7,110,570 B1 | 9/2006 | Berenz et al. | |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,319,779 B1 | 1/2008 | Mummareddy et al. | |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,757,171 B1 | 7/2010 | Wong et al. | |
| 7,826,657 B2 | 11/2010 | Zhang et al. | |
| 7,830,570 B2 | 11/2010 | Morita et al. | |
| 7,881,493 B1 | 2/2011 | Edwards et al. | |
| 7,921,036 B1 | 4/2011 | Sharma | |
| 8,010,458 B2 | 8/2011 | Galbreath et al. | |

(56) References Cited

U.S. PATENT DOCUMENTS

| | | | |
|---|---|---|---|
| 8,022,831 B1* | 9/2011 | Wood-Eyre | B60T 7/14 |
| | | | 180/272 |
| 8,219,438 B1* | 7/2012 | Moon | G06Q 30/0201 |
| | | | 705/7.29 |
| 8,300,891 B2 | 10/2012 | Chen et al. | |
| 8,369,608 B2 | 2/2013 | Gunaratne | |
| 8,401,248 B1 | 3/2013 | Moon et al. | |
| 8,442,638 B2 | 5/2013 | Libbus et al. | |
| 8,522,779 B2 | 9/2013 | Lee et al. | |
| 8,600,120 B2 | 12/2013 | Gonion et al. | |
| 8,640,021 B2 | 1/2014 | Perez et al. | |
| 8,947,217 B2 | 2/2015 | Moussa et al. | |
| 9,723,992 B2* | 8/2017 | Senechal | G06F 19/3418 |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman | |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0060728 A1 | 3/2003 | Mandigo | |
| 2003/0093784 A1 | 5/2003 | Dimitrova et al. | |
| 2003/0191682 A1 | 10/2003 | Shepard et al. | |
| 2003/0191816 A1 | 10/2003 | Landress et al. | |
| 2004/0181457 A1 | 9/2004 | Biebesheimer | |
| 2004/0183685 A1* | 9/2004 | Strumolo | G08B 21/06 |
| | | | 340/575 |
| 2005/0187437 A1 | 8/2005 | Matsugu | |
| 2005/0283055 A1 | 12/2005 | Shirai et al. | |
| 2005/0289582 A1 | 12/2005 | Tavares et al. | |
| 2006/0019224 A1 | 1/2006 | Behar et al. | |
| 2006/0143647 A1 | 6/2006 | Bill | |
| 2006/0149428 A1 | 7/2006 | Kim et al. | |
| 2006/0235753 A1 | 10/2006 | Kameyama | |
| 2007/0060830 A1* | 3/2007 | Le | A61B 5/0476 |
| | | | 600/544 |
| 2007/0167689 A1 | 7/2007 | Ramadas et al. | |
| 2007/0173733 A1* | 7/2007 | Le | G16H 40/63 |
| | | | 600/544 |
| 2007/0210902 A1* | 9/2007 | Stewart | B60Q 1/484 |
| | | | 340/435 |
| 2007/0239787 A1 | 10/2007 | Cunningham et al. | |
| 2007/0255831 A1 | 11/2007 | Hayashi et al. | |
| 2007/0265507 A1 | 11/2007 | de Lemos | |
| 2007/0299964 A1 | 12/2007 | Wong et al. | |
| 2008/0059570 A1 | 3/2008 | Bill | |
| 2008/0091512 A1 | 4/2008 | Marci et al. | |
| 2008/0091515 A1 | 4/2008 | Thieberger et al. | |
| 2008/0101660 A1 | 5/2008 | Seo | |
| 2008/0103784 A1 | 5/2008 | Wong et al. | |
| 2008/0184170 A1 | 7/2008 | Periyalwar | |
| 2008/0208015 A1 | 8/2008 | Morris et al. | |
| 2008/0221472 A1 | 9/2008 | Lee et al. | |
| 2008/0287821 A1 | 11/2008 | Jung et al. | |
| 2008/0292151 A1 | 11/2008 | Kurtz et al. | |
| 2009/0002178 A1 | 1/2009 | Guday et al. | |
| 2009/0006206 A1 | 1/2009 | Groe | |
| 2009/0083421 A1 | 3/2009 | Glommen et al. | |
| 2009/0094286 A1 | 4/2009 | Lee et al. | |
| 2009/0112694 A1 | 4/2009 | Jung et al. | |
| 2009/0112810 A1 | 4/2009 | Jung et al. | |
| 2009/0133048 A1 | 5/2009 | Gibbs et al. | |
| 2009/0150919 A1 | 6/2009 | Lee et al. | |
| 2009/0156907 A1 | 6/2009 | Jung et al. | |
| 2009/0164132 A1* | 6/2009 | Jung | G16B 45/00 |
| | | | 702/19 |
| 2009/0209829 A1 | 8/2009 | Yanagidaira et al. | |
| 2009/0210290 A1 | 8/2009 | Elliott et al. | |
| 2009/0217315 A1 | 8/2009 | Malik et al. | |
| 2009/0259518 A1 | 10/2009 | Harvey | |
| 2009/0270170 A1 | 10/2009 | Patton | |
| 2009/0271417 A1 | 10/2009 | Toebes et al. | |
| 2009/0299840 A1 | 12/2009 | Smith | |
| 2009/0318776 A1* | 12/2009 | Toda | A61B 5/18 |
| | | | 600/301 |
| 2010/0070523 A1 | 3/2010 | Delgo et al. | |
| 2010/0099955 A1 | 4/2010 | Thomas et al. | |
| 2010/0134302 A1 | 6/2010 | Ahn et al. | |
| 2010/0266213 A1 | 10/2010 | Hill | |
| 2010/0274847 A1 | 10/2010 | Anderson et al. | |
| 2010/0324437 A1 | 12/2010 | Freeman | |
| 2011/0126226 A1 | 5/2011 | Makhlouf | |
| 2011/0134026 A1 | 6/2011 | Kang et al. | |
| 2011/0143728 A1 | 6/2011 | Holopainen et al. | |
| 2011/0144971 A1 | 6/2011 | Danielson | |
| 2011/0196855 A1 | 8/2011 | Wable et al. | |
| 2011/0231240 A1 | 9/2011 | Schoen et al. | |
| 2011/0251493 A1 | 10/2011 | Poh et al. | |
| 2011/0263946 A1 | 10/2011 | el Kaliouby et al. | |
| 2012/0109452 A1 | 5/2012 | Autran et al. | |
| 2012/0324491 A1 | 12/2012 | Bathiche et al. | |
| 2013/0023337 A1 | 1/2013 | Bowers et al. | |
| 2013/0116587 A1 | 5/2013 | Sornmo et al. | |
| 2013/0197409 A1 | 8/2013 | Baxter et al. | |
| 2013/0328684 A1* | 12/2013 | Chang | G08B 21/06 |
| | | | 340/575 |
| 2014/0171752 A1 | 6/2014 | Park et al. | |
| 2014/0172910 A1* | 6/2014 | Jung | G06F 16/68 |
| | | | 707/769 |
| 2014/0192325 A1* | 7/2014 | Klin | A61B 5/16 |
| | | | 351/209 |
| 2015/0213634 A1* | 7/2015 | Karmarkar | G06T 11/60 |
| | | | 345/589 |
| 2015/0258995 A1 | 9/2015 | Essers et al. | |
| 2016/0104486 A1* | 4/2016 | Penilla | H04L 67/12 |
| | | | 704/232 |
| 2017/0003784 A1* | 1/2017 | Garg | A63F 13/87 |
| 2017/0014050 A1* | 1/2017 | Klin | A61B 5/16 |
| 2017/0337438 A1* | 11/2017 | el Kaliouby, Jr. | A61B 5/0077 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

(56) References Cited

OTHER PUBLICATIONS

Albiol, Alberto, et al. "Face recognition using HOG-EBGM." Pattern Recognition Letters 29.10 (2008): 1537-1543.

* cited by examiner

US 10,482,333 B1

MENTAL STATE ANALYSIS USING BLINK RATE WITHIN VEHICLES

RELATED APPLICATIONS

This application is a continuation-in-part of U.S. patent application "Mental State Analysis Using Blink Rate for Vehicles" Ser. No. 15/670,791, filed Aug. 7, 2017, which claims the benefit of U.S. provisional patent applications "Image Analysis Framework using Remote Learning with Deployable Artifact" Ser. No. 62/439,928, filed Dec. 29, 2016, "Audio Analysis Learning using Video Data" Ser. No. 62/442,325, filed Jan. 4, 2017, "Vehicle Manipulation using Occupant Image Analysis" Ser. No. 62/448,448, filed Jan. 20, 2017, "Smart Toy Interaction using Image Analysis" Ser. No. 62/442,291, filed Jan. 4, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, and "Image Analysis for Emotional Metric Generation" Ser. No. 62/524,606, filed Jun. 25, 2017.

The application "Mental State Analysis Using Blink Rate for Vehicles" Ser. No. 15/670,791, filed Aug. 7, 2017 is also continuation-in-part of U.S. patent application "Mental State Analysis Using Blink Rate" Ser. No. 14/214,918, filed Mar. 15, 2014, which claims the benefit of U.S. provisional patent applications "Mental State Analysis Using Blink Rate" Ser. No. 61/789,038, filed Mar. 15, 2013, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Well Being Monitoring" Ser. No. 61/798,731, filed Mar. 15, 2013, "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014.

The application "Mental State Analysis Using Blink Rate" Ser. No. 14/214,918, filed Mar. 15, 2014, is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The application "Mental State Analysis Using Blink Rate for Vehicles" Ser. No. 15/670,791, filed Aug. 7, 2017 is also a continuation-in-part of U.S. patent application "Computer Based Convolutional Processing for Image Analysis" Ser. No. 15/666,048, filed Aug. 1, 2017, which claims the benefit of U.S. provisional patent applications "Deep Convolutional Neural Network Analysis of Images for Mental States" Ser. No. 62/370,421, filed Aug. 3, 2016, "Image Analysis Framework using Remote Learning with Deployable Artifact" Ser. No. 62/439,928, filed Dec. 29, 2016, "Audio Analysis Learning using Video Data" Ser. No. 62/442,325, filed Jan. 4, 2017, "Vehicle Manipulation using Occupant Image Analysis" Ser. No. 62/448,448, filed Jan. 20, 2017, "Smart Toy Interaction using Image Analysis" Ser. No. 62/442,291, filed Jan. 4, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, and "Image Analysis for Emotional Metric Generation" Ser. No. 62/524,606, filed Jun. 25, 2017.

The application "Computer Based Convolutional Processing for Image Analysis" Ser. No. 15/666,048, filed Aug. 1, 2017 is also a continuation-in-part of U.S. patent application "Image Analysis using Sub-sectional Component Evaluation to Augment Classifier Usage" Ser. No. 15/395,750, filed Dec. 30, 2016, which claims the benefit of U.S. provisional patent applications "Image Analysis Using Sub-Sectional Component Evaluation to Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Image Analysis using Sub-sectional Component Evaluation to Augment Classifier Usage" Ser. No. 15/395,750, filed Dec. 30, 2016, is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF ART

This application relates generally to analysis of mental states and more particularly to mental state analysis using eye blink rates for vehicles.

BACKGROUND

People spend a tremendous amount of time traveling in vehicles. Travel times include daily commuting to and from the office, taking the kids to soccer practice and piano lessons, taking the pets to the veterinary, shopping, traveling, and the many other common activities that require transportation. Depending on where people live, they use a variety of vehicles to meet their transportation needs. The vehicles can range from cars and motorcycles; to buses, trains and subways; to ride and ride sharing services; and even to unmotorized vehicles such as bicycles. Traveling is time consuming at best, and at worst, boring, frustrating, irritating, and stressful. Rush hour traffic, accidents, bad or rude drivers, and poorly maintained roads, among other inevitabilities, further complicate vehicular transportation. The difficulties of transportation are also compounded by operating an unfamiliar vehicle, driving in an unfamiliar city, navigating an unfamiliar public transportation network, and even by having to remember to drive on the opposite side of the road. These challenges surrounding transportation can have catastrophic consequences. Irritated operators of vehicles can experience road rage and other antisocial behaviors, while bored, sleepy, tired, impaired, distracted, or inattentive drivers can cause vehicular accidents and injury to themselves, pedestrians, bicyclists, animals, and property.

Transportation in general, and particularly urban transportation, present many design, management, and fiscal problems which can directly impact travelers. Heavily congested surface roads and highways, and woefully insufficient parking, directly influence the mental states, moods, and emotions of travelers. The congested roadways cause longer, more dangerous commutes, and the lack of available parking increases the amount of time wasted looking for a place to leave a vehicle. Public transportation presents challenges of its own, such as overfilled buses, trains, and subways during commuting hours, and underused routes due to lack of interest, poor planning, and other factors. The increased use of bicycles presents its own challenges when vehicles and bicycles share overfilled roadways that were not originally designed for multi-use scenarios. While vehicle operators and passengers may not be directly involved in the management and financing of transportation systems, they are the ones who directly experience the frustration and annoyance of using the transportation systems, all while carrying the tax burden of paying to build, operate, maintain, and upgrade them.

SUMMARY

The mental states that can be experienced by an individual present themselves in externally detectable manifestations. The mental states can range widely from happy to sad, calm to angry, engaged to bored, among many others. The detectable manifestations of these mental states include facial expressions, eye blink rates, and physiological parameters such as heart rate, sweating, changes to respiration, and blood pressure. The mental state or states of a person are influenced by many types of external stimuli. One increasingly common source of external stimuli results from operating or traveling in a vehicle. People frequently spend 300 or more hours per year traveling in vehicles. Vehicle operation, traffic, and distractions such as cellphones, the content on the radio, and other drivers, can all impact moods, emotions, and mental states of vehicle occupants. Capturing a holistic view of the occupants of a given vehicle can provide an understanding of the emotional, physiological, and mental states they are experiencing. Capturing holistic occupant data can lead to increases in road safety and to improvement in the overall transportation experience of the occupants in the given vehicle. Collecting data and learning about the vehicle operator and passenger behaviors enables adaptation of vehicle operating characteristics and vehicle environmental experiences for the operators and passengers.

Disclosed is a technique for mental state analysis that includes obtaining video of an individual within a vehicle. The individual can be operating a vehicle such as a car or motorcycle, or a passenger in a vehicle such as a bus, train, subway, or airplane. The collected video is analyzed, using one or more processors, to determine eye blink information for the individual, such as eye blink rate, eye blink duration, and eye blink frequency. One or more mental states of the individual are inferred based on the eye blink information. The mental states can include frustration, confusion, disappointment, hesitation, cognitive overload, focusing, engagement, exploration, confidence, trust, delight, disgust, skepticism, doubt, satisfaction, excitement, laughter, calmness, stress, anger, happiness, and curiosity. A computer-implemented method for mental state analysis is disclosed comprising obtaining video of an individual; analyzing, using one or more processors, the video to detect a blink event based on a classifier for a blink that was determined wherein the blink event is determined by: locating a portion of a face with eyes; performing temporal analysis on the portion of the face; and identifying that the eyes are closed for a frame in the video using the temporal analysis; evaluating a blink duration of the individual for the blink event; determining blink-rate information using the blink event and one or more other blink events; compensating the blink-rate information for a context; evaluating blinking for a group of people of which the individual is a part; determining a difference in blinking between the individual and a remainder of the group; and inferring mental states of the individual for the blink event, wherein the mental states are based on the blink event, the blink duration of the individual, the difference in blinking between the individual and the remainder of the group, and the blink-rate information that was compensated. In embodiments, the video of the individual is obtained from within a vehicle. In embodiments, the method further comprises manipulating the vehicle based on the mental states that were inferred. In embodiments, the inferring of mental states may include one or more of attention, concentration, boredom, fatigue, or cognitive load. In embodiments, the inferring of mental states may indicate drowsiness for the individual.

In embodiments, a computer program product embodied in a non-transitory computer readable medium for mental state analysis, the computer program product comprising code which causes one or more processors to perform operations of: obtaining video of an individual within a vehicle with an image capture device; analyzing, using one or more processors, the video to detect a blink event based on a classifier for a blink that was determined wherein the blink event is determined by identifying that eyes of the individual are closed for a frame in the video using temporal analysis; evaluating, using the one or more processors, a blink duration of the individual for the blink event; determining, using the one or more processors, blink-rate information using the blink event and one or more other blink events; compensating, using the one or more processors, the blink-rate information for a context; and inferring, using the one or more processors, mental states of the individual for the blink event, wherein the mental states are based on the blink event, the blink duration of the individual, and the blink-rate information that was compensated.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
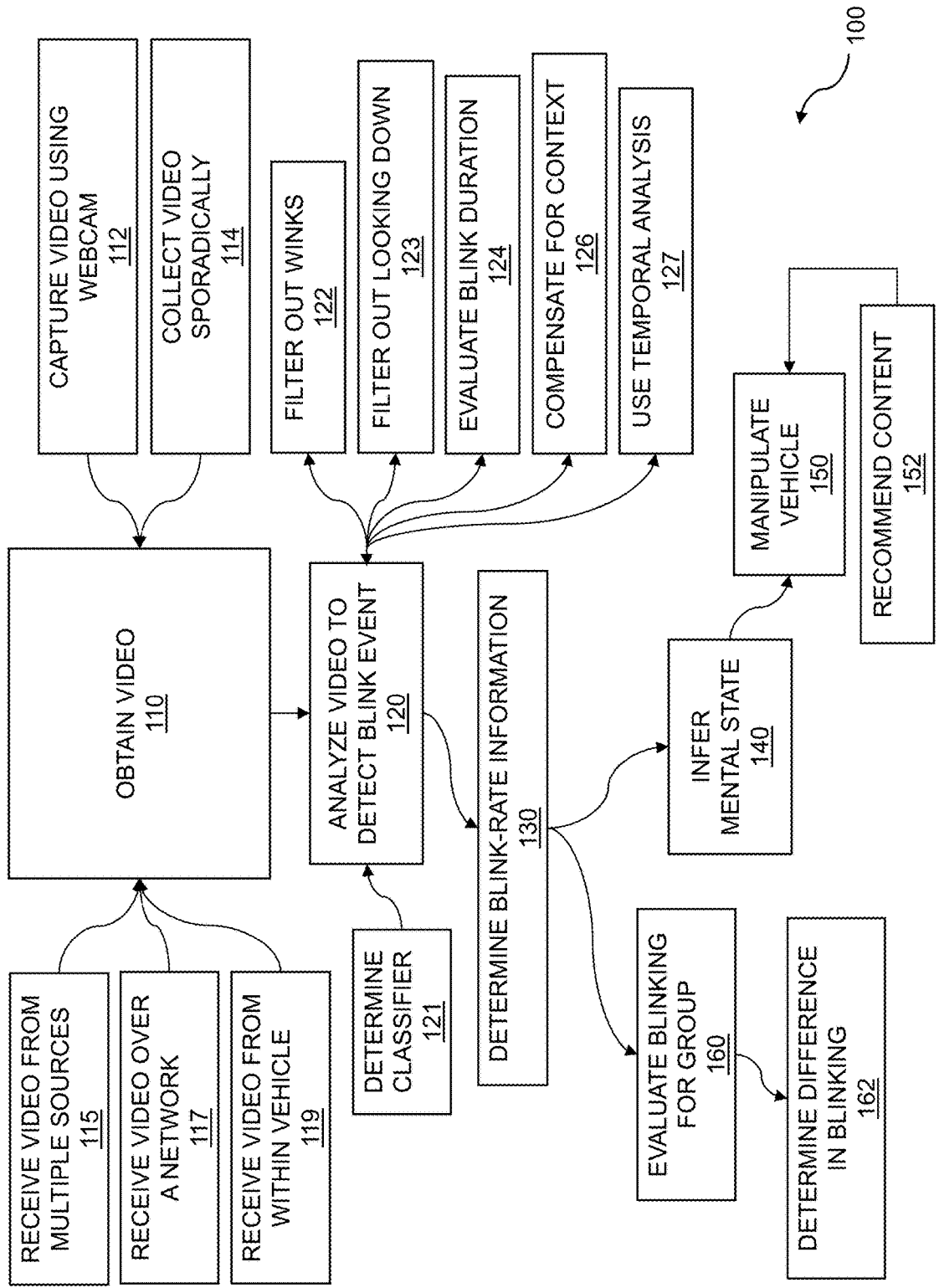
FIG. 1 is a flow diagram for blink rate and mental state analysis.

The mental state or mental states of an individual can be observed through such external manifestations as the actions and/or behaviors of an individual. External manifestations that can be related to mental states include facial movements such as smiling, frowning, grimacing, smirking, and laughing. Some of these facial movements can be conscious movements, while others are subconscious movements. Other external manifestations of mental state can be subtler. One such manifestation of a person's mental state is an additional facial movement. The additional facial movement can include eye blink events. That is, one or more of the rate at which an individual blinks her or his eyes, the duration of a single eye blink, the average duration of eye blinks, and the average eye blink duration compared to that of other people, can be related to the mental state of an individual. Eye blink event analysis can be used to detect or identify drowsiness, impairment, distractedness, and other mental states. These and other mental states can be potentially dangerous when the individual is engaging in activities such as operating machinery, operating a motor vehicle, and so on.

Eye blink events can be related to cognitive load. Eye blink rates can decrease as cognitive load increases. Cognitive load can refer to the total amount of mental effort that an individual expends while performing a given task or tasks. The task can include learning, problem solving, memorizing, multitasking, and so on. Cognitive load can vary from individual to individual, and from task to task. Generally, the more difficult or complicated the task, the greater the cognitive load the individual can experience. When cognitive load is low, the individual may be able to address multiple tasks and easily handle and ignore distractions. When cognitive load is high, the individual may have great difficulty handling one task, let alone more than one task, or ignoring distractions. Cognitive load can include three factors, where the factors can include intrinsic load, extraneous load, and germane load. Intrinsic cognitive load can refer to the cognitive load associated with or intrinsic to a certain topic. Extraneous cognitive load can refer to the presentation of tasks to an individual such as a learner. Germane cognitive load can refer to the amount of cognitive effort put into creating a permanent knowledge store relating to task performance and other operations.

Other eye blink rates can be related to drowsiness. Drowsiness can be determined based on eye blink rates decreasing, and the duration of eyelid closure increasing. Drowsiness or somnolence can include a mental state in which an individual has a strong desire to sleep. Drowsiness can include a mental state that can precede the individual falling into a sleep state. Drowsiness can be an indicator that an individual is unfit to operate machinery, operate a motor vehicle, or other tasks which require that the individual be alert. Drowsiness can be due to a variety of factors including lack of sleep, physical health, medications, illicit drugs, and other factors. While a range of treatments can be applied to drowsiness, the presence of drowsiness as a mental state of an individual can be used to make recommendations to the individual such as to not operate machinery or a motor vehicle, to not engage in complex tasks, to not engage in potentially hazardous actives, and so on.

Further eye blink rates can be related to fatigue. Eye blink rates can decrease as fatigue increases. Fatigue can include eye fatigue, where eye fatigue can result from long periods of time on a tasks (ToT), viewing a computer screen or television, operating a motor vehicle, and so on. Fatigue can include tiredness and can occur gradually. The effects of fatigue can generally be reversed by the individual getting rest or getting treatment for medical conditions. Fatigue can be based on physical causes and mental causes. Physical causes of fatigue can result from strenuous physical activity and can result in the muscles of an individual being unable to operate at an optimal level of physical performance. Mental fatigue can result from intense mental activity and can cause a diminution of cognitive performance. Fatigue can result from hard, physical labor or long hours at the office, mental stress, overstimulation, under stimulation, active recreation, jet lag, ennui, depression, disease, sleep deprivation, etc. Fatigue may also result from chemical causes such as vitamin or mineral deficiencies and poisoning. Fatigue can result from afflictions such as the common cold or influenza, and medical conditions such as anemia.

Other eye blink rates can be related to other factors as an individual operates a motor vehicle or travels in a motor vehicle. An individual operating machinery or a motor vehicle can experience a range of mental states, where the mental states can include one or more of frustration, confusion, disappointment, hesitation, cognitive overload, focusing, engagement, exploration, confidence, trust, delight, disgust, skepticism, doubt, satisfaction, excitement, laughter, calmness, stress, sadness, anger, happiness, and curiosity. Similarly, an individual traveling in a motor vehicle can experience a similar variety of mental states. Monitoring the eye blink rates of the vehicle operator and the eye blink rates of the vehicle passenger can provide indications of the one or more mental states of the operator and of the passenger. As discussed, slowing eye blink rates of the operator can indicate operator mental states such as drowsiness, fatigue, distractedness, inebriation, alertness, attention, and so on. Eye blink rates of the passenger can indicate mental states such as those just discussed for the operator, nervousness, boredom, and so on.

An individual's mental state can be impacted by his or her interaction with a computer or display associated with a computing device, such as an on-board computer within a vehicle. Understanding the individual's mental state during such interactions can be valuable for a variety of reasons, such as improving the program that the individual is using, rating a media presentation, or optimizing an advertisement. Traditional methods of monitoring an individual's mental state often do not provide an effective way to monitor the individual's mental state during his or her interaction with a computer, for a variety of reasons. For example, surveys or rating systems are prone to non-participation and inaccurate reporting, and even though physiological information can in some instances provide an accurate measure of mental state, traditional physiological monitoring devices are intrusive and not available at most computer workstations.

In contrast, a webcam is able to unobtrusively monitor an individual as they interact with the computer. Many computer systems today already include a webcam, and for systems that do not already have one, a webcam can be easily and inexpensively added to nearly any modern computer workstation. An individual can interact with a computer to view a media presentation or to perform some type of task on the computer while being monitored by a webcam. In some embodiments, some other type of image capture device, for example, a security camera or a camera on a mobile device such as a tablet or a smartphone, is used to monitor the individual in place of, or in addition to, the webcam. The video from the webcam is then analyzed to determine eye blink information. The eye blink information can include eye-blink rate, eye-blink duration, time between blinks, and/or other information related to one or more eye blinks by the individual being monitored.

Once the eye blink information is determined, the eye blink information can be correlated with context, for example, the activity being performed by the user, demographic information about the user such as the user's age and/or gender, the time of day, the brightness of the screen and/or environment, or other contextual information. In some embodiments, the eye-blink information is compensated, or adjusted, based on the context. The eye blink information can then be used to infer the mental state of the individual, which is correlated to context in some embodiments. The mental state can be used to modify the activity being performed, a game being played, a choice of advertisement to be displayed, a media presentation, or some other activity. In some embodiments, an output is rendered to display the mental states and/or eye blink information, which can be correlated with the context, such as the timeline of a media presentation.

FIG. 1 is a flow diagram for blink rate and mental state analysis. The flow 100 describes a computer-implemented method for mental state analysis and begins by obtaining video 110 of an individual within a vehicle with an image capture device. In some embodiments, the video is captured using a webcam 112. Other types of video capture devices can be used for obtaining the video of the individual. In embodiments, wherein the image capture device includes a near-infrared image capture device. The near-infrared image capture device can capture video that can include near-infrared video. The near-infrared video captured by the near-infrared image capture device can include images in low ambient light conditions. The near-infrared image capture device can capture physiological information for the individual such as elevated body temperature due to illness, irritation, or anger. The video, whether visible-light video, near-infrared video, etc., can be captured continuously or can be captured sporadically 114 due to the individual moving outside of the camera's field of view, limited storage space, or a lack of interest in an individual's mental state during a particular time period, among other reasons that warrant a cessation of recording. The video can also be captured from multiple sources 115, for example, by additional cameras such as cameras in a mobile device, security cameras, or other cameras. In some embodiments, the video is received over a network 117, such as the internet, from another computer. In some embodiments, the video is received from within a vehicle 119.

The flow 100 further comprises analyzing the video 120 to detect a blink event. A blink event can start with an eye being open but starting to close. The blink event can conclude with the eye opening or going back to its normal state. The analysis of the video can include detecting on each frame of the video, or portion of the video, whether an eye is open, closed, or in between. By analyzing surrounding frames, and possibly the video as a whole, a blink can be differentiated from a wink, sleeping or relaxing, looking down, and the like. The analyzing can comprise determining a classifier 121 for a blink in order to identify eye blinks in the video. In some embodiments, the blink event is detected using the classifier. The analyzing can filter out single eye winks 122 as eye winks sometimes represent a conscious act and may not be a reliable indicator of mental state. The analyzing can filter out looking down 123 by the individual. As the individual looks down, the individual's eyes can give an appearance of blinking, depending on the position of the camera, even if the eyes do not actually blink. Likewise, eye closures, which are longer than blinks, can be filtered. In at least some embodiments, the classifier is configured to do the filtering and differentiation for winks, looking down, and eye closures. In embodiments, the blink event is determined by identifying that eyes of the individual are closed for a frame in the video using temporal analysis 127.

The video is analyzed for information in addition to eye blink-rate information in some embodiments. For example, the flow 100 can further comprise evaluating blink duration 124 because the length of time that an individual's eyes are closed can be indicative of one or more mental states. Some embodiments further comprise evaluating average blink duration. The blink-rate information can include information on blink duration. Some embodiments further comprise determining context for the individual. Some embodiments determine context directly from the video, such as lighting conditions, number of people in the room, or other context. Additional context can be gathered from other sources such as direct input by the user, login credentials, the programs currently running, file names being accessed, various types of sensors such as thermometers, a route being traveled, amount of traffic being encountered, glare on a windshield, or the computer's clock/calendar, among other inputs. Some embodiments include compensating blink-rate information for a context 126. For example, the brightness of the monitor or room can have an impact on the blink-rate that is unrelated to the individual's mental state, and therefore can be compensated for in order that the eye blink-rate may more accurately reflect the mental state of the individual.

The flow 100 includes using the blink event and one or more other blink events to determine blink-rate information 130. The blink-rate information can include a number of blinks over a period of time, a total number of blinks, and so on. The blink-rate information can be based on a blink rate of an individual, an aggregate blink rate for a group of people, and the like. The blink-rate information can include a blink duration. The flow 100 further comprises inferring mental states of the individual based on the eye blink-rate information 140. The inferring can be based on the blink duration. The inferring of mental states can include one or more of attention, concentration, boredom, or fatigue. In some embodiments, the inferring of mental states includes one or more mental states of frustration, confusion, disappointment, hesitation, cognitive overload, focusing, engagement, exploration, confidence, trust, delight, disgust, skepticism, doubt, satisfaction, excitement, laughter, calmness, stress, sadness, anger, happiness, and curiosity. While various values of eye blink-rates and/or durations, as well as changes in the eye blink-rates and/or durations, can be indicative of various mental states, a higher blink rate can indicate a mental state of being focused. In some embodiments, the inferring can include evaluation of an impaired state, such as being ill or under the influence of alcohol or drugs.

In embodiments, the inferring can be used to manipulate a vehicle 150. Many various manipulations can occur. The manipulating of the vehicle can include recommending action. The manipulating of the vehicle can include one or more of initiating a locking out operation, recommending a break for an occupant, recommending a different route, recommending how far to drive, controlling the vehicle in response to traffic, adjusting seats, adjusting mirrors, adjusting climate control, adjusting lighting, and so on. In embodiments, the manipulating of the vehicle can include recommending content 152 to the individual. The recommending content to the individual can include adjusting music, generating audio stimuli, activating a braking system, or activating steering control. The flow 100 further includes evaluating blinking for a group 160 of people of which the individual is a part. The evaluating blinking of the group can include aggregating, averaging, or otherwise combining blinking for the group. The blinking of the group can be useful for determining an average blink rate for a given blink event, a blink duration, a blink frequency, etc. The flow 100 further includes determining a difference in blinking 162 between the individual and a remainder of the group. The difference in blinking can result from differences in mental states such as drowsiness, impairment, distractedness, or other mental states The video obtained from within a vehicle can be of the driver of the vehicle. Typically, the driver of a vehicle will have the most direct control over the vehicle. However, the video obtained from within a vehicle can be of a passenger in the vehicle. A passenger can also have great influence over the control of a vehicle, albeit indirectly. In an autonomously driven vehicle, such as a self-driving car, there is not be a driver, per se. Instead, the autonomous vehicle can be operated by a driver, where the driver is a custodial driver, a backup driver, a safety driver, or the like. At other times, the autonomous vehicle can be carrying only one of more passengers. Such passenger video may be critical to safe and smooth operation of an autonomously driven vehicle. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
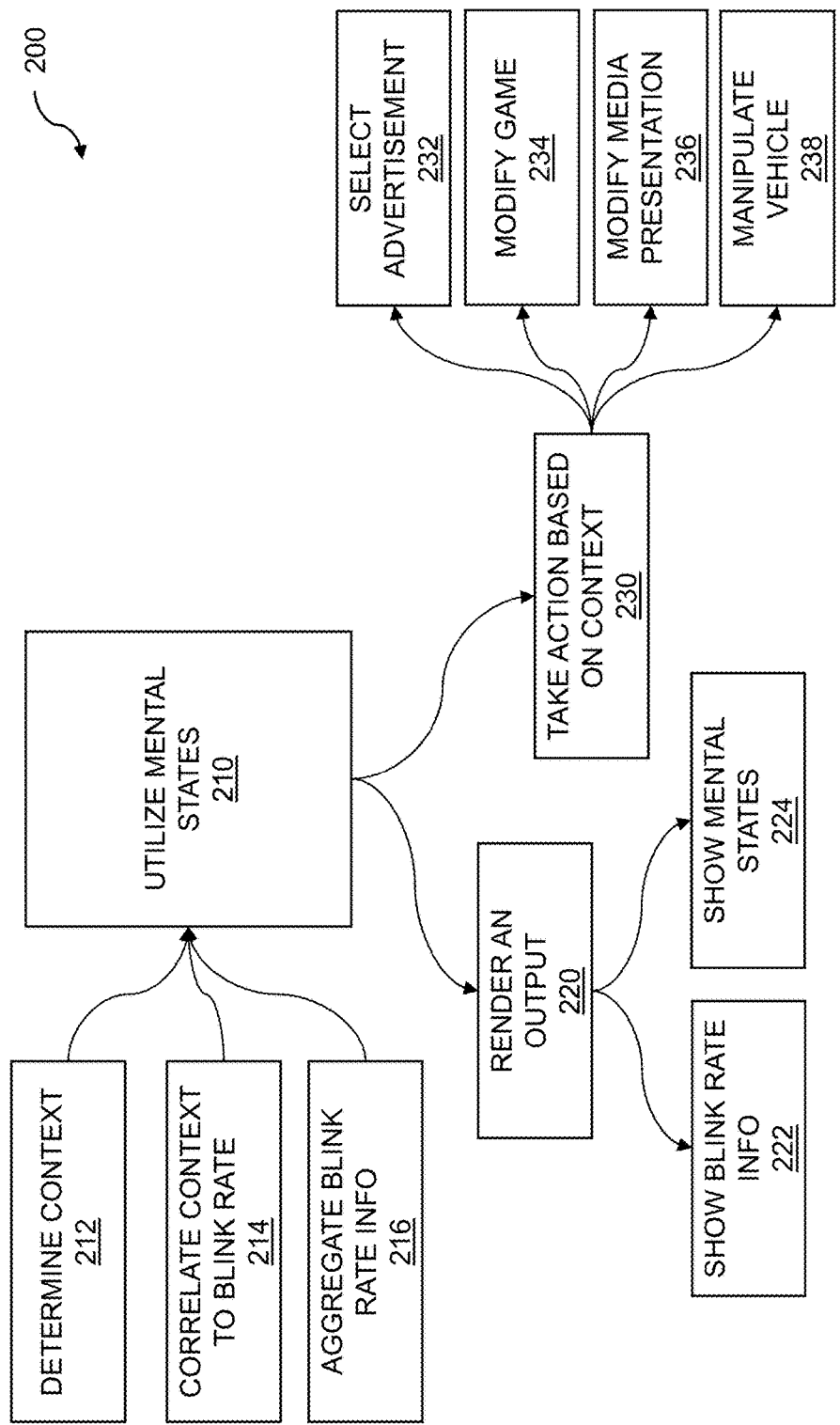
FIG. 2 is a flow diagram for mental state usage.

FIG. 2 is a flow diagram for mental state usage. A flow 200 can continue from or be part of the previous flow 100. The mental state usage can be based on mental state analysis using blink rate within vehicles. The flow 200 includes utilizing mental state information 210 for one or more purposes. Some embodiments determine context 212 for use in conjunction with the mental state information. The context can include one or more of screen brightness, environmental brightness, gender, and demographics. In some embodiments, the context includes information about the task being performed, the media being presented, or the game being played. The context can vary over time. In some embodiments, the flow 200 can include correlating the context to the eye blink-rate information 214 to allow relationships between the contexts, the blink-rate information, and/or other mental state information to be determined. Thus, the blink-rate information can be correlated with activities performed by the individual. In some embodiments, the flow 200 comprises aggregating the blink-rate information 216 for the individual with blink-rate information for a plurality of other people.

Some embodiments use the mental state information to render an output 220. The output can include the eye blink-rate information 222 and/or the mental states 224 which were inferred. The output display correlation between the blink-rate information and a stimulus which the individual is encountering. The mental states, which were inferred, can be correlated to a context for the individual. In some embodiments, the mental states and/or the context trigger an action to be taken 230. The actions which can be taken based on inferred mental state include selecting an advertisement 232, modifying a game 234, modifying a media presentation 236, manipulating a vehicle 238, or the like. Various steps in the flow 200 may be changed in order, repeated, omitted, or the like without departing from the disclosed concepts. Various embodiments of the flow 200 may be included in a computer program product embodied in a non-transitory computer readable medium that includes code executable by one or more processors.

Figure 3:
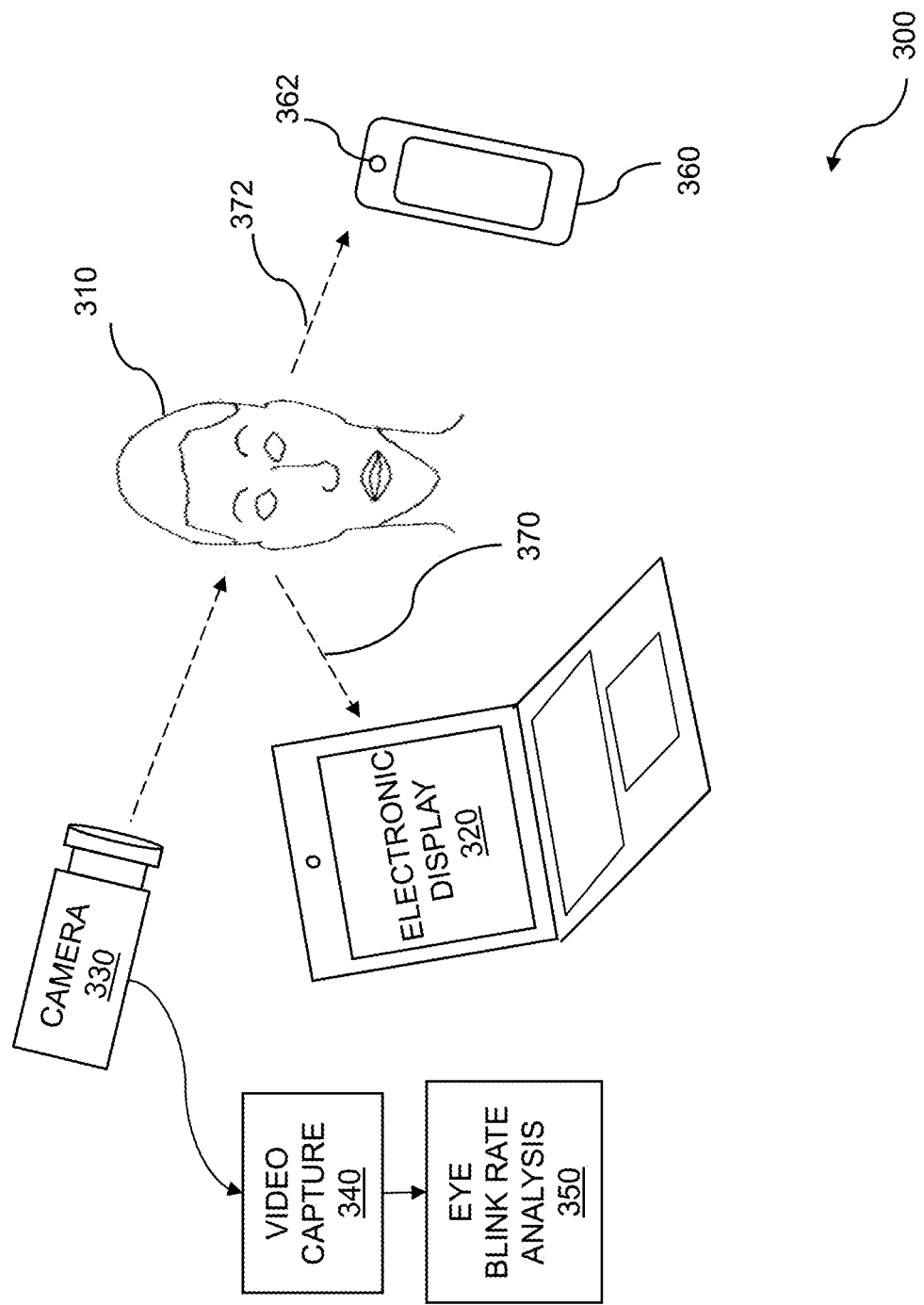
FIG. 3 is an example image collection system for facial analysis.

FIG. 3 is an image collection system for facial analysis 300. Facial analysis can support mental state analysis, where the mental state analysis can use blink rate within vehicles. The facial analysis can include analyzing video obtained of an individual within a vehicle, where the analyzing can detect a blink event. A blink duration can be evaluated for the blink event, and blink-rate information can be determined using the blink event and one or more other blink events. The blink-rate information can be compensated for a context. Mental states of the individual can be inferred for the blink event, where the mental states are based on the blink event, the blink duration of the individual, and the blink-rate information that was compensated.

An individual 310 can view 370 an electronic display 320 and mental state data (such as eye blink-rate information) on the individual 310 can be collected and analyzed. The electronic display 320 can show an output of a computer application that the individual 310 is using, or the electronic display 320 can show a media presentation so that the individual 310 is exposed to the media presentation. The display 320 can be any electronic display, including but not limited to, a computer display, a laptop screen, a net-book screen, a tablet screen, a cell phone display, a mobile device display, a remote with a display, a television, a projector, or the like. Likewise, other electronic displays can be viewed 372 such as a mobile device showing the media presentation and so on. The media presentation can include one of a group consisting of a movie, a television show, a web series, a webisode, a video, a video clip, an electronic game, an e-book, or an e-magazine. The electronic display 320 can be a part of, or can be driven from, the device collecting the mental state data, or the electronic display might only be loosely coupled with, or even unrelated to, the device collecting the mental state data, depending on the embodiment. The collecting can be accomplished with a mobile device 360 such as a cell phone, a tablet computer, or a laptop computer, and the mobile device can include a front-side camera 362. The facial data can be collected with a camera such as the front-side camera 362 of the mobile device 360 and/or by a webcam 330. Thus, the video can be obtained using a webcam 330. The video can be obtained from multiple sources, and in some embodiments, at least one of the multiple sources is a mobile device. The eye blink-rate information can be collected intermittently when the individual 310 is looking in the direction of a camera such as the front facing mobile camera 362 or the webcam 330. The camera can also capture images of the setting that can be used in determining contextual information.

The webcam 330 can capture video, audio, and/or still images of the individual 310. A webcam, as the term is used herein, can include a video camera, a still camera, a thermal imager, a CCD device, a phone camera, a three-dimensional camera, a depth camera, multiple webcams used to show different views of a person, or any other type of image capture apparatus that can allow captured data to be used in an electronic system. The images of the person 310 from the webcam 330 can be captured by a video capture unit 340. In some embodiments, video is captured, while in others, one or more still images are captured. The system 300 can include analyzing the video for eye blink-rate information 350, eye blink duration, facial data, and/or physiological data. The facial data includes information on facial expressions, action units, head gestures, smiles, smirks, brow furrows, squints, lowered eyebrows, raised eyebrows, or attention, in various embodiments. Analysis of physiological data can also be performed based on the video. Respiration, heart rate, heart rate variability, perspiration, temperature, and other physiological indicators of mental state can be determined by analyzing the video.

Figure 4:
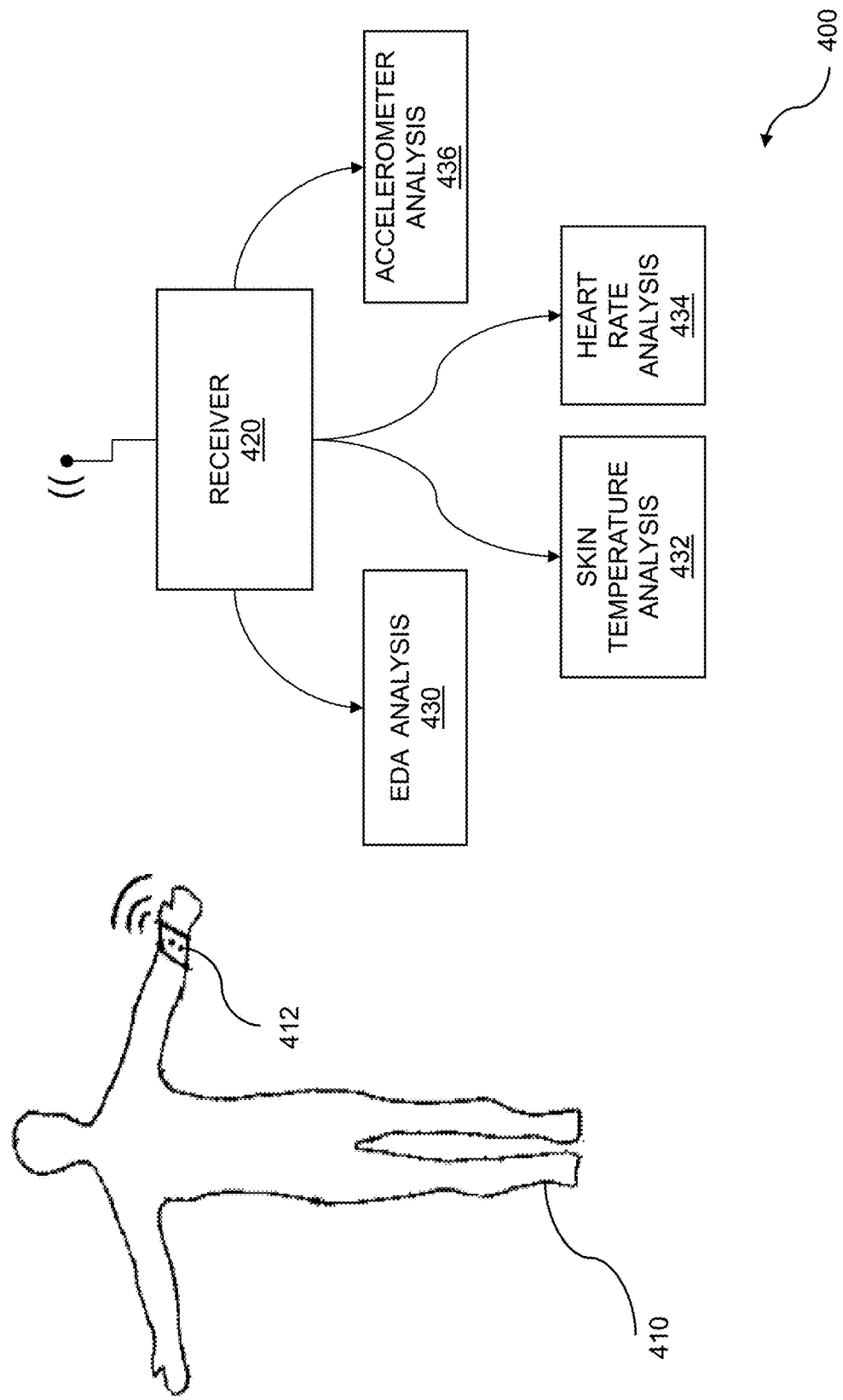
FIG. 4 is a diagram for sensor analysis.

FIG. 4 is a diagram for sensor analysis which can be used to assist or augment mental state analysis using blink rate within vehicles. A system 400 can analyze data collected from a person 410 as he or she interacts with a computer, a media presentation, a vehicle, and so on. The person 410 can have a biosensor 412 attached to him or her for the purpose of collecting mental state data. The biosensor 412 can be placed on the wrist, palm, hand, head, or other part of the body. In some embodiments, multiple biosensors are placed on the body in multiple locations. The biosensor 412 can include detectors for physiological data, which can include one or more of heart rate, heart rate variability, blink rate, skin temperature, and respiration. The biosensor 412 can transmit collected information to a receiver 420 using wireless technology such as Wi-Fi, Bluetooth, 802.11, cellular, or another band. In other embodiments, the biosensor 412 communicates with the receiver 420 by other methods, such as a wired or optical interface. The receiver can provide the data to one or more components in the system 400. In some embodiments, the biosensor 412 records multiple types of physiological information in memory for later download and analysis. In some embodiments, the download of recorded physiological data is accomplished through a USB port or another wired or wireless connection.

A process for mental state analysis can comprise collecting physiological data or accelerometer data with a biosensor. Mental states can be inferred based on physiological data (such as the physiological data captured by the sensor 412) along with blink-rate information. Mental states can also be inferred based, in part, on facial expressions and head gestures observed by a webcam or a combination of data from the webcam along with data from the sensor 412. The mental states can be analyzed based on arousal and valence. Arousal can range from being highly activated, such as when someone is agitated, to being entirely passive, such as when someone is bored. Valence can range from being very positive, such as when someone is happy, to being very negative, such as when someone is angry. Physiological data can include one or more of electrodermal activity (EDA), heart rate, heart rate variability, skin temperature, respiration, skin conductance or galvanic skin response (GSR), accelerometer readings, and other types of analysis of a human being. It will be understood that both here and elsewhere in this document, physiological information can be obtained either by biosensor 412 or by facial observation via the webcam 330.

Electrodermal activity can also be collected. The electrodermal activity can be analyzed 430 to indicate arousal, excitement, boredom, or other mental states based on observed changes in skin conductance. Skin temperature can also be collected and/or recorded on a periodic basis and in turn can be analyzed 432. Changes in skin temperature can indicate arousal, excitement, boredom, or other mental states. Heart rate information can be collected and recorded and can also be analyzed 434. A high heart rate can indicate excitement, arousal, or another mental state. Accelerometer data can be collected and used to track one, two, or three dimensions of motion. The accelerometer data can be recorded. The accelerometer data can be used to create an actigraph showing an individual's activity level over time. The accelerometer data can be analyzed 436 and can indicate a sleep pattern, a state of high activity, a state of lethargy, or another state. The various data collected by the biosensor 412 can be used along with the eye blink-rate information captured by the webcam in the analysis of mental state. Contextual information can also be based on one or more of skin temperature or accelerometer data.

Figure 5:
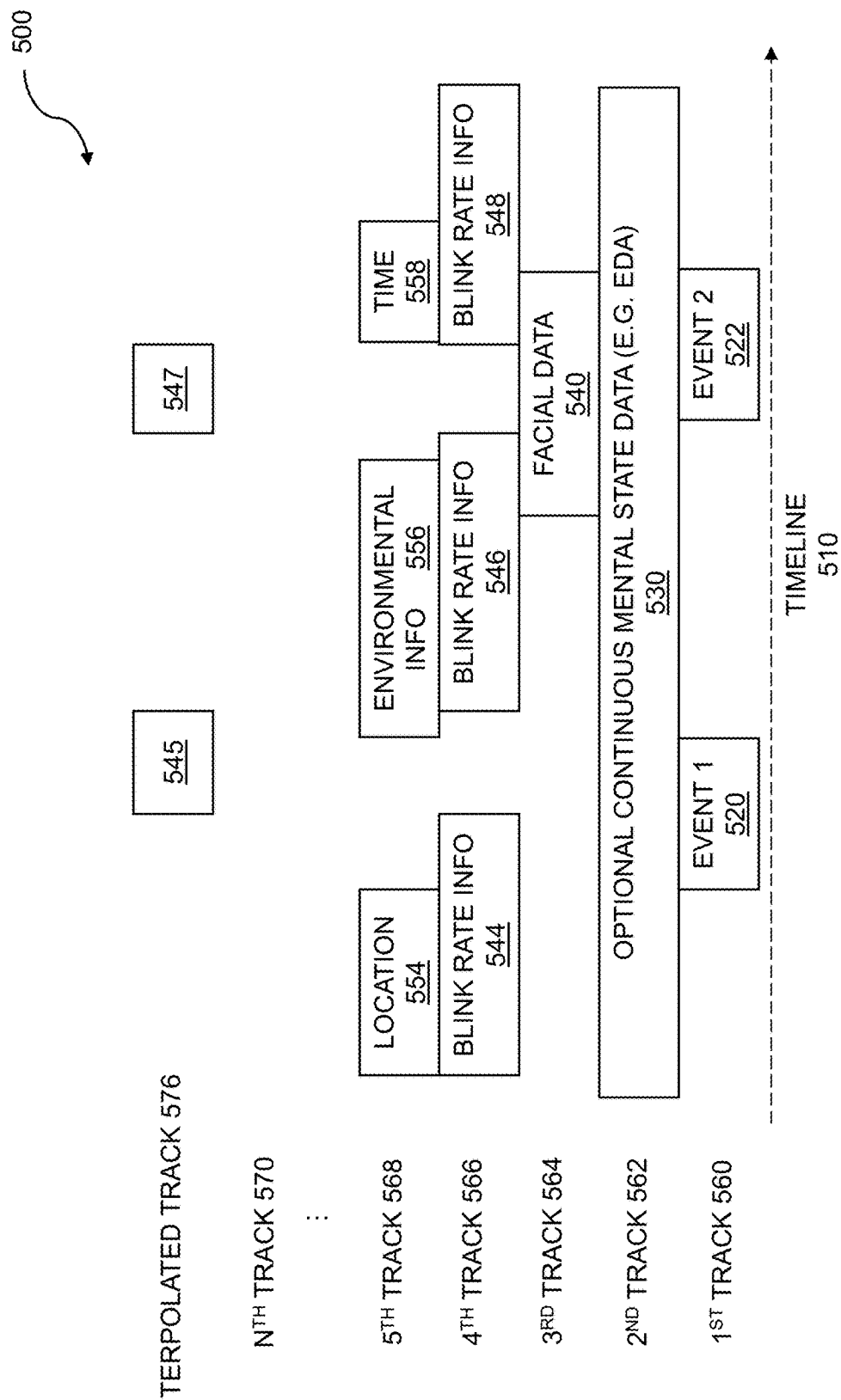
FIG. 5 shows an example timeline with information tracks relating to mental states.

FIG. 5 shows an example timeline 510 with information tracks 500 relating to mental states. The mental states can be inferred from blink events based on mental state analysis using blink rate within vehicles. The timeline can allow various data to be correlated, such as blink-rate information and contextual information. A first track 560 shows events that can be related to the individual's use of a computer. A first event 520 marker on the timeline can indicate an action that the individual took (such as launching an application); an action initiated by the computer (such as the presentation of a dialog box); an external event (such as a new global positioning system [GPS] coordinate); receiving an e-mail, phone call, or text message; or any other type of event. In some embodiments, a photograph is used to document an event or simply save contextual information in the first track 560. A second event 522 marker can indicate another action or event. Such event markers can be used to provide contextual information and may include data about emails, text messages, phone logs, file names, or any other information that can be useful in understanding the context of a user's actions.

A second track 562 can include continuously collected mental state data such as electrodermal activity data 530. A third track 564 can include mental state data such as facial data 540, which can be collected on an intermittent basis by a first camera (although in some embodiments the facial data is collected continuously). The facial data can be collected intermittently when the individual is looking toward a camera. The facial data 540 can include one or more still photographs, videos, or abstracted facial expressions, which can be collected when the user looks in the direction of the camera.

A fourth track 566 can include eye blink-rate information which can be determined using video. The video is collected sporadically, in some embodiments, so the blink-rate information may not be continuous. A first set of blink-rate information 544 can be determined for a first period of time, a second set of blink-rate information 546 can be determined for a second period of time, and a third set of blink-rate information 548 can be determined for a third period of time.

A fifth track 568 can include contextual data, which is collected along with the collection of the mental state data. In the example shown, the fifth track 568 includes location 554, environmental information 556, and time 558, although other types of contextual data can be collected in other embodiments. In the embodiment shown, the fifth track 568 allows contextual data to be associated with, and correlated to, the fourth track 566 containing the eye blink-rate information. Some analysis can evaluate and combine multiple tracks of additional data associated with one or more tracks of mental state data. For example, another track can include identity information about the individual being monitored by a camera, in embodiments, the same camera that captures the third track 564 or the fourth track 566 of mental state data.

Additional tracks, through the $n^{th}$ track 570, of mental state data or additional data of any type can be collected. The additional tracks 570 can be collected on a continuous or on an intermittent basis. The intermittent basis can be either occasional or periodic. Analysis can further comprise interpolating mental state data when the mental state data collected is intermittent, and/or imputing additional mental state data where the mental state data is missing. One or more interpolated tracks 576 can be included and can be associated with mental state data that can be collected on an intermittent basis, such as the eye blink-rate data of the fourth track 566. Interpolated data 545 and a second instance of interpolated data 547 can contain interpolations of the eye blink-rate data of the fourth track 566 for the time periods where no blink-rate data was collected in that track. Other embodiments can interpolate data for periods where other types of information are missing. In other embodiments, analysis includes interpolating mental state analysis when the collected mental state data is intermittently available.

Figure 6:
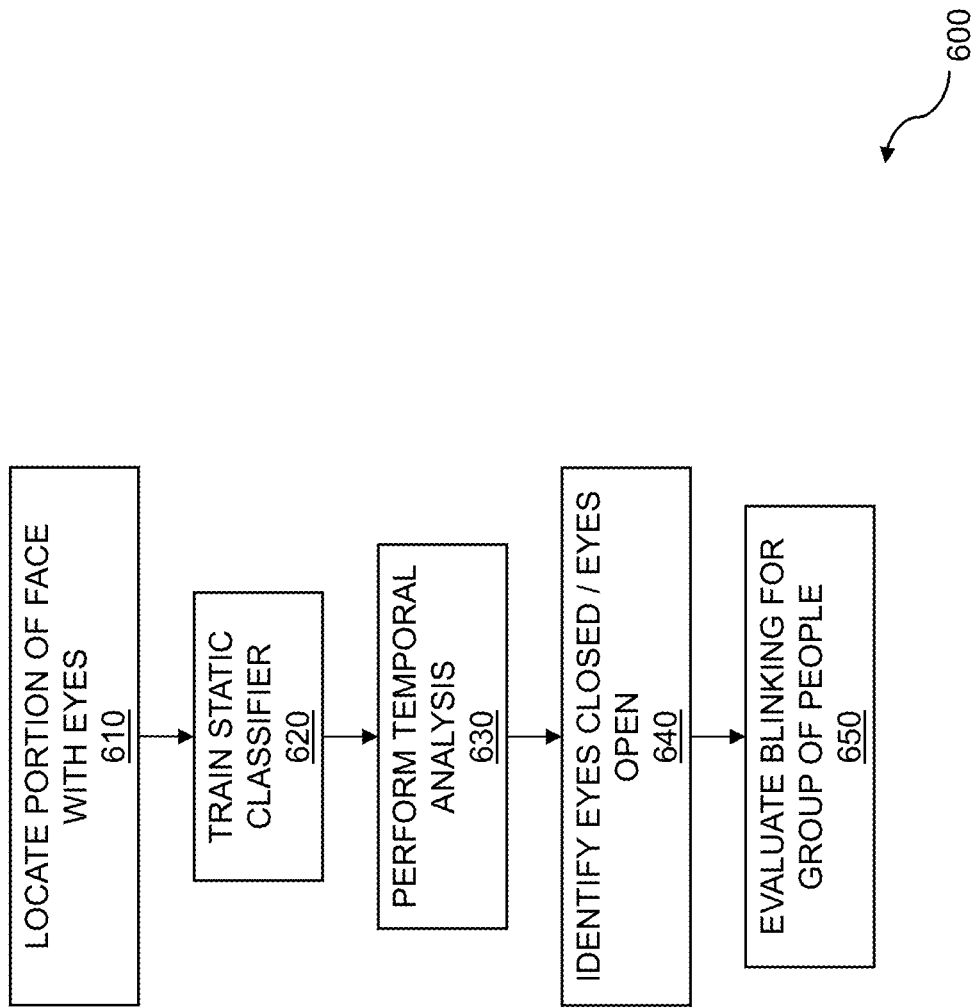
FIG. 6 is a flow diagram for blink analysis.

FIG. 6 is a flow diagram for blink analysis. Blink analysis can include mental state analysis using blink rate within vehicles. A flow 600 can continue from or be part of the previous flow 100 or flow 200, or flow 600 can be performed independently of flow 100 to provide additional data analysis. The flow 600 can be used to aid in blink event determination and includes locating a portion of a face with eyes 610. The boundaries of the eyes, eyelids, and other portions of the face can be used to identify the needed portion. In embodiments, the flow 600 includes training a static classifier 620 to aid in the determination of when the eyes blink. The classifier can be trained off line using numerous images or videos. The classifier can be downloaded from a database for use in the blink analysis. The static classifier can identify when there are open eyes. The static classifier can identify when there are closed eyes. The flow 600 includes performing temporal analysis 630 on the portion of the face. Frame-by-frame analysis can be performed. In embodiments, 30 frames per second are obtained from the video. In most cases, a blink involves eyes closing for a single frame of a video. The flow 600 includes identifying that the eyes are closed 640 for a frame of the video using the temporal analysis.

In embodiments, the flow 600 includes evaluating blinking for a group of people 650 of which the individual is a part. If a group of people are simultaneously viewing an event, a video, or another media presentation, then the group of people will often blink at the same time. The blinking can occur at a scene change, a lighting change, and so on. If someone is not paying attention, then the person's blinking can occur at different times from those who are paying attention. The method can include evaluating synchronicity of blinking for the group. In some embodiments, the method includes determining a difference in blinking between the individual and a remainder of the group. The difference can be used to determine a mental state for the individual. In some cases, the mental state includes lacking attention. In embodiments, the flow can include determining a difference in blinking by the individual and typical blinking for the individual. A history can be accumulated that indicates a typical blink rate and/or a typical blink duration by the individual. A difference from typical can be used to evaluate fatigue, cognitive load, and other factors in mental states. In some embodiments, the inferring mental states of the individual is based on the difference in blinking by the individual and typical blinking for the individual. Various steps in the flow 600 may be changed in order, repeated, omitted, or the like without departing from the disclosed concepts. Various embodiments of the flow 600 may be included in a computer program product embodied in a non-transitory computer readable medium that includes code executable by one or more processors.

Figure 7:
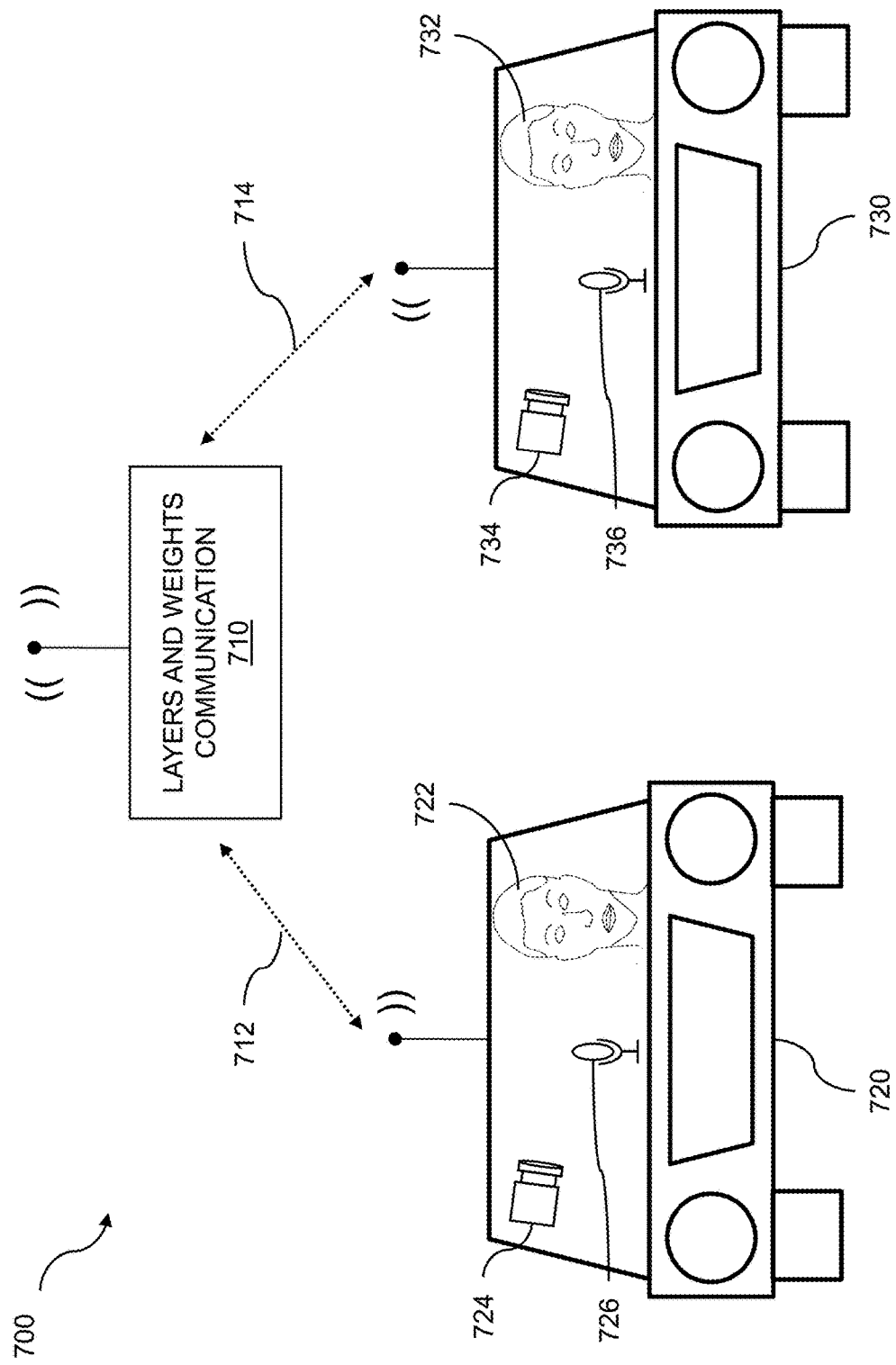
FIG. 7 is a system diagram for vehicle artificial intelligence evaluation.

FIG. 7 is a system diagram for vehicle artificial intelligence evaluation. Video data and audio data can be collected from an individual for mental state analysis. The mental state analysis can use blink rate to infer one or more mental states. Cameras, microphones, and other sensors can be used for collecting video and audio from occupants within vehicles. The video can include facial data, and the audio can include voice data. The video and audio can include physiological data, and so on. The video can be analyzed using a classifier to detect a blink event, and a blink duration can be evaluated based on the blink event. Blink-rate information can be determined using the blink event and one or more other blink events, and the blink-rate information can be compensated for a context. Mental states of the individual can be inferred for the blink event, where the mental states are based on the blink event, the blink duration, and the compensated blink-rate information.

A system diagram for mental state analysis 700 is shown. The system can include mental state data, mental state information, and layers and weights communication 710. The communicating mental state data can include mental state data including facial data and voice data that can be collected from an individual. The communicating of the layers and weights can include sending adjusted levels and adjusted weights to a first vehicle 720, to a second vehicle 730, and so on.

The layers and weights can be sent to a first vehicle 720 using a wireless link 712 or other data transfer technique. The mental state data and mental state information can be sent over the same wireless link 712 or a different wireless link. The layers and weights that can be sent can be based on mental state data including facial data from an occupant 722 of the vehicle 720. The mental state data including facial data can be collected using a camera 724 or other image capture technique. The system 700 can include collecting voice data and augmenting the mental state data with the voice data. The voice data can be collected from the occupant 722 using a microphone 726 or other audio capture technique. The voice data can include audio data, where the audio data can include traffic sounds, road noise, music that can be played by the occupant, and so on. The system 700 can include evaluating the voice data for timbre, prosody, vocal register, vocal resonance, pitch, loudness, speech rate, or language content. The evaluating the voice data can also be used in evaluating the mental state or states of the occupant 722 of the vehicle 720. In embodiments, the augmenting can be based on lexical analysis of the voice data that looks at sentiment. As for the first vehicle, the mental state profile can be sent to a second vehicle 730 using a wireless link 714 or other data transfer technique. The mental state profile can be based on mental state data including facial data from an occupant 732 of the vehicle 730, can be based on the mental state data including facial data from the occupant 722 of the first vehicle 720, and so on. The mental state data including facial data can be collected using a camera 734 or other image capture technique. The system 700 can include collecting voice data from the occupant 732 using a microphone 736 or other audio capture technique.

Figure 8:
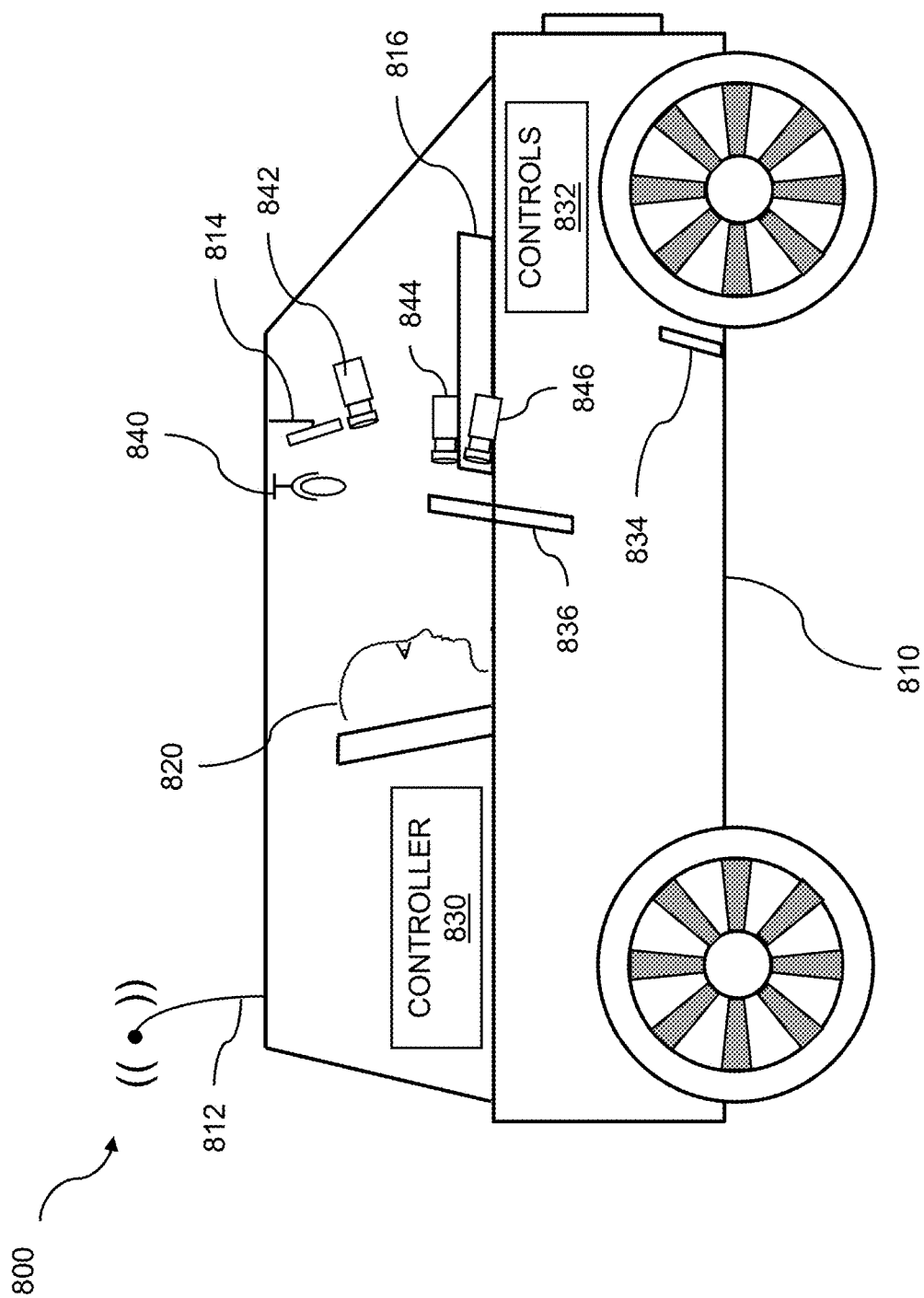
FIG. 8 is a system diagram for an interior of a vehicle

FIG. 8 is a system diagram for an interior of a vehicle 800. Video data and audio data obtained from an individual within a vehicle can be analyzed to detect a blink event. Mental state analysis can use blink rate of one or more individuals within vehicles. Mental state analysis can infer mental states by using the blink event. The blink event can include a blink, a blink duration, blink rate, and so on. Cameras within vehicles are used to obtain video of an individual, and microphones within vehicles can be used for collecting voice data. The video is analyzed based on a classifier to detect a blink event, and a blink duration of the individual is evaluated for the blink event. Blink-rate information is determined using the blink event and one or more other blink events, and the blink-rate information is compensated for a context. Mental states of the individual are inferred for the blink event, where the mental states are based on the blink event, the blink duration, and the compensated blink-rate information. One or more occupants of a vehicle 810, such as occupant 820, can be observed using a microphone 840, one or more cameras 842, 844, or 846, and other audio and image capture techniques. The image data can include video data. The video data and the audio data can include mental state data, where the mental state data can include facial data, voice data, physiological data, and the like. The occupant can be a driver 820 of the vehicle 810, a passenger within the vehicle, and so on. In embodiments, the driver can be a custodial driver The cameras or imaging devices that can be used to obtain images including facial data from the occupants of the vehicle 810 can be positioned to capture the face of the vehicle operator, the face of a vehicle passenger, multiple views of the faces of occupants of the vehicle, and so on. The cameras can be located near a rear-view mirror 814 such as camera 842, positioned near or on a dashboard 816 such as camera 844, positioned within the dashboard such as camera 846, and so on. The microphone or audio capture device 840 can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 810 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 810 can include standard controls such as a steering wheel 836, a throttle control (not shown), a brake 834, and so on. The interior of the vehicle can include other controls 832 such as controls for seats, mirrors, climate controls, audio systems, etc. The controls 832 of the vehicle 810 can be controlled by a controller 830. The controller 830 can control the vehicle 810 in various manners such as autonomously, semi-autonomously, assertively to a vehicle occupant 820, etc. In embodiments, the controller provides vehicle control or manipulation techniques, assistance, etc. The controller 830 can receive instructions via an antenna 812 or use other wireless techniques. The controller 830 can be preprogrammed to cause the vehicle to follow a specific route. The specific route that the vehicle is programmed to follow can be based on the mental state of the vehicle occupant. The specific route can be chosen based on lowest stress, least traffic, most scenic view, shortest route, and so on.

Figure 9:
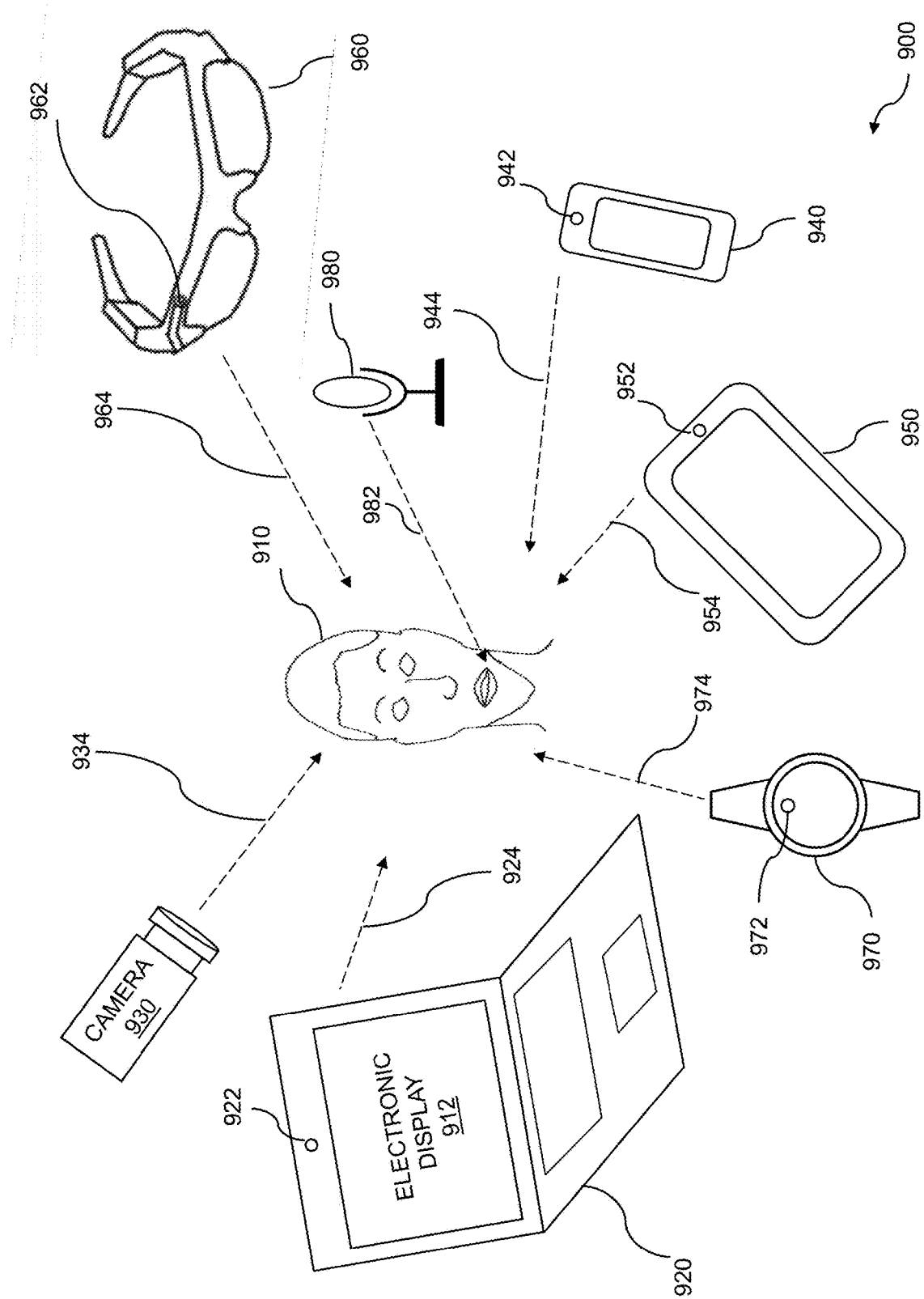
FIG. 9 is a diagram showing image collection and audio collection including multiple mobile devices.

FIG. 9 is a diagram showing image collection including multiple mobile devices. Image data and audio data can be collected using multiple mobile devices. The collected images can be analyzed to detect a blink event, and a blink duration can be evaluated for the blink event. Blink-rate information can be determined, and the blink-rate information can be compensated for a context. Mental states of the individual can be inferred for the blink event. Mental state analysis can use blink rates within vehicles. While one person is shown, in practice the video data or audio data on any number of people can be obtained. In the diagram 900, the multiple mobile devices can be used separately or in combination to collect video data, audio data, or both video data and audio data on a user 910. While one person is shown, the video data and audio data can be collected on multiple people. A user 910 can be observed as she or he is performing a task, experiencing an event, viewing a media presentation, and so on. The user 910 can be shown one or more media presentations, political presentations, social media, or another form of displayed media. The one or more media presentations can be shown to a plurality of people. The media presentations can be displayed on an electronic display 912 or another display. The data collected on the user 910 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 910 can be analyzed and viewed for a variety of purposes including expression analysis, cognitive state analysis, mental state analysis, emotional state analysis, and so on. The electronic display 912 can be on a laptop computer 920 as shown, a tablet computer 950, a cell phone 940, a television, a mobile monitor, or any other type of electronic device. In one embodiment, video data including expression data is collected on a mobile device such as a cell phone 940, a tablet computer 950, a laptop computer 920, or a watch 970. Similarly, the audio data including speech data and non-speech vocalizations can be collected on one or more of the mobile devices. Thus, the multiple sources can include at least one mobile device, such as a phone 940 or a tablet 950, or a wearable device such as a watch 970 or glasses 960. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 922, a phone camera 942, a tablet camera 952, a wearable camera 962, and a mobile camera 930. A wearable camera can comprise various camera devices, such as a watch camera 972. Sources of audio data 982 can include a microphone 980.

As the user 910 is monitored, the user might move due to the nature of the task, boredom, discomfort, distractions, or for another reason. As the user moves, the camera with a view of the user's face can be changed. Thus, as an example, if the user is looking in a first direction, the line of sight 924 from the webcam 922 is able to observe the user's face, but if the user is looking in a second direction, the line of sight 934 from the mobile camera 930 is able to observe the user's face. Furthermore, in other embodiments, if the user is looking in a third direction, the line of sight 944 from the phone camera 942 is able to observe the user's face, and if the user is looking in a fourth direction, the line of sight 954 from the tablet camera 952 is able to observe the user's face. If the user is looking in a fifth direction, the line of sight 964 from the wearable camera 962, which can be a device such as the glasses 960 shown and can be worn by another user or an observer, is able to observe the user's face. If the user is looking in a sixth direction, the line of sight 974 from the wearable watch-type device 970, with a camera 972 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 910 can also use a wearable device including a camera for gathering contextual information and/or collecting expression data on other users. Because the user 910 can move her or his head, the facial data can be collected intermittently when she or he is looking in a direction of a camera. In some cases, multiple people can be included in the view from one or more cameras, and some embodiments include filtering out faces of one or more other people to determine whether the user 910 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 10:
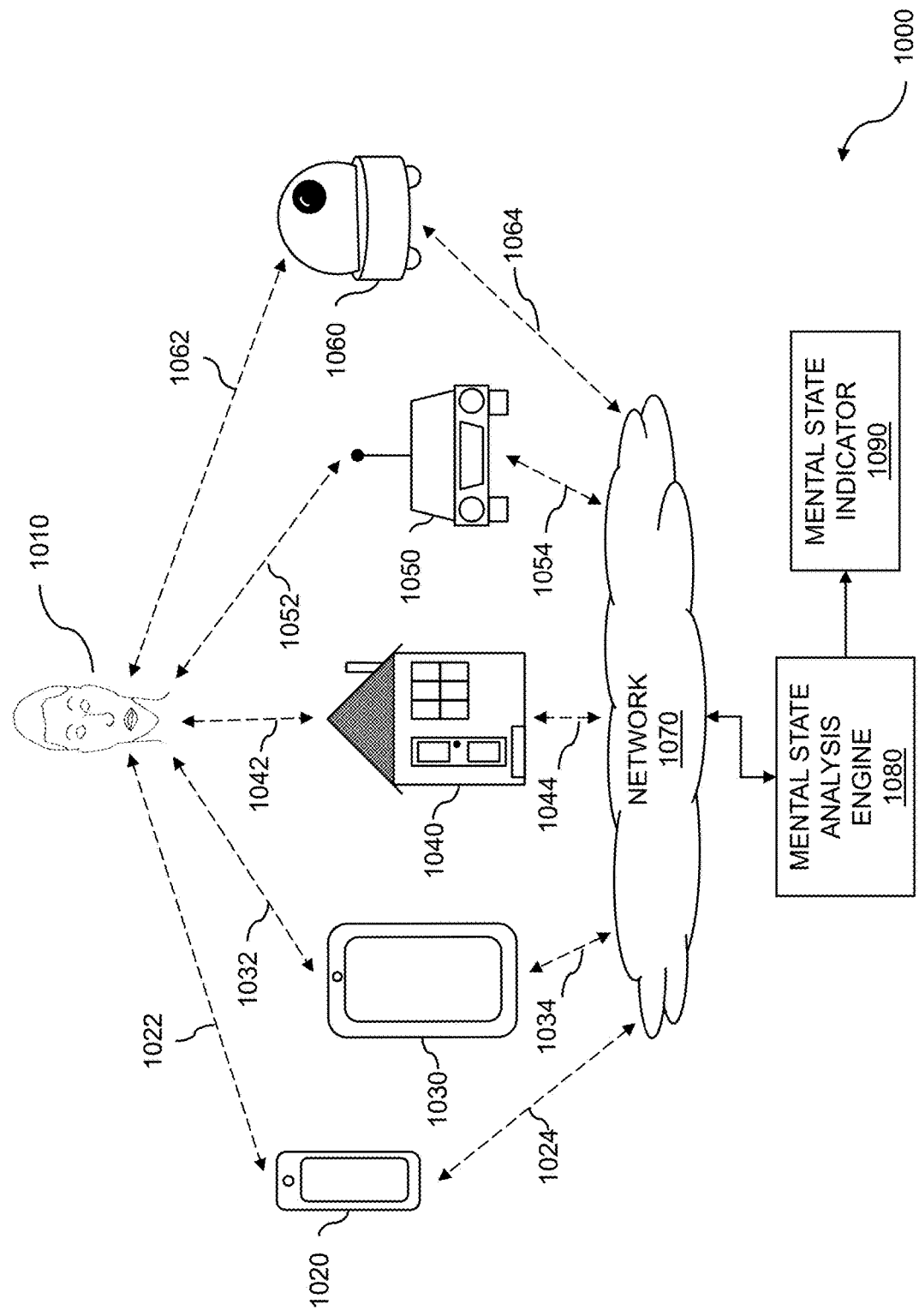
FIG. 10 illustrates image collection and audio collection including devices and locations.

FIG. 10 illustrates image collection and audio collection including devices and locations. Cameras, microphones, and other devices can be used to collect video data, audio data, and other data collected from an individual. The video data, audio data, and other data can be analyzed to detect a blink event. Mental state analysis can infer mental states by using the blink event. The blink event can include a blink, a blink duration, blink rate, and so on. Images can be obtained for mental state analysis using blink rate within vehicles. Images that can include image data and facial data are collected from a user within a vehicle. Processors are used to analyze the video such as image data and media presentation, and to evaluate blink duration. Blink-rate information is determined using the blink event and one or more other blink events. The blink-rate information is compensated for a context, and mental states of the individual are inferred for the blink event.

In the diagram 1000, the multiple mobile devices, vehicles, and locations, can be used singly or together to collect video data on a user 1010. While one person is shown, the video data can be collected on multiple people. A user 1010 can be observed as she or he is performing a task, experiencing an event, viewing a media presentation, and so on. The user 1010 can be shown one or more media presentations, political presentations, social media, or another form of displayed media. The one or more media presentations can be shown to a plurality of people. The media presentations can be displayed on an electronic display coupled to a client device. The data collected on the user 1010 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1010 can be analyzed and viewed for a variety of purposes including expression analysis, mental state analysis, and so on. The electronic display can be on a smartphone 1020 as shown, a tablet computer 1030, a personal digital assistant, a television, a mobile monitor, or any other type of electronic device. In one embodiment, expression data is collected on a mobile device such as a cell phone 1020, a tablet computer 1030, a laptop computer, or a watch. Thus, the multiple sources can include at least one mobile device, such as a phone 1020 or a tablet 1030, or a wearable device such as a watch or glasses (not shown). A mobile device can include a front-side camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1010, data can be collected in a house 1040 using a web camera or the like; in a vehicle 1050 using a web camera, client device, etc.; by a social robot 1060, and so on.

As the user 1010 is monitored, the user 1010 might move due to the nature of the task, boredom, discomfort, distractions, or for another reason. As the user moves, the camera with a view of the user's face can be changed. Thus, as an example, if the user 1010 is looking in a first direction, the line of sight 1022 from the smartphone 1020 is able to observe the user's face, but if the user is looking in a second direction, the line of sight 1032 from the tablet 1030 is able to observe the user's face. Furthermore, in other embodiments, if the user is looking in a third direction, the line of sight 1042 from a camera in the house 1040 is able to observe the user's face, and if the user is looking in a fourth direction, the line of sight 1052 from the camera in the vehicle 1050 is able to observe the user's face. If the user is looking in a fifth direction, the line of sight 1062 from the social robot 1060 is able to observe the user's face. If the user is looking in a sixth direction, a line of sight from a wearable watch-type device, with a camera included on the device is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1010 can also use a wearable device including a camera for gathering contextual information and/or collecting expression data on other users. Because the user 1010 can move her or his head, the facial data can be collected intermittently when she or he is looking in a direction of a camera. In some cases, multiple people can be included in the view from one or more cameras, and some embodiments include filtering out faces of one or more other people to determine whether the user 1010 is looking toward a camera. All or some of the expression data can be continuously or sporadically available from the various devices and other devices.

The captured video data can include facial expressions and can be transferred over the network 1070 such as the Internet. The smartphone 1020 can share video using link 1024, the tablet 1030 using link 1034, the house 1040 using link 1044, the vehicle 1050 using link 1054, and the social robot 1060 using link 1064. The links 1024, 1034, 1044, 1054, and 1064 can be wired, wireless, and hybrid links. The captured video data, including facial expressions, can be analyzed on a mental state analysis engine 1080, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capture device. The analysis data from the mental state analysis engine can be processed by a mental state indicator 1090. The mental state indicator 1090 can indicate mental states, moods, emotions, etc. In embodiments, the emotions can include of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, sadness, poignancy, or mirth.

Figure 11:
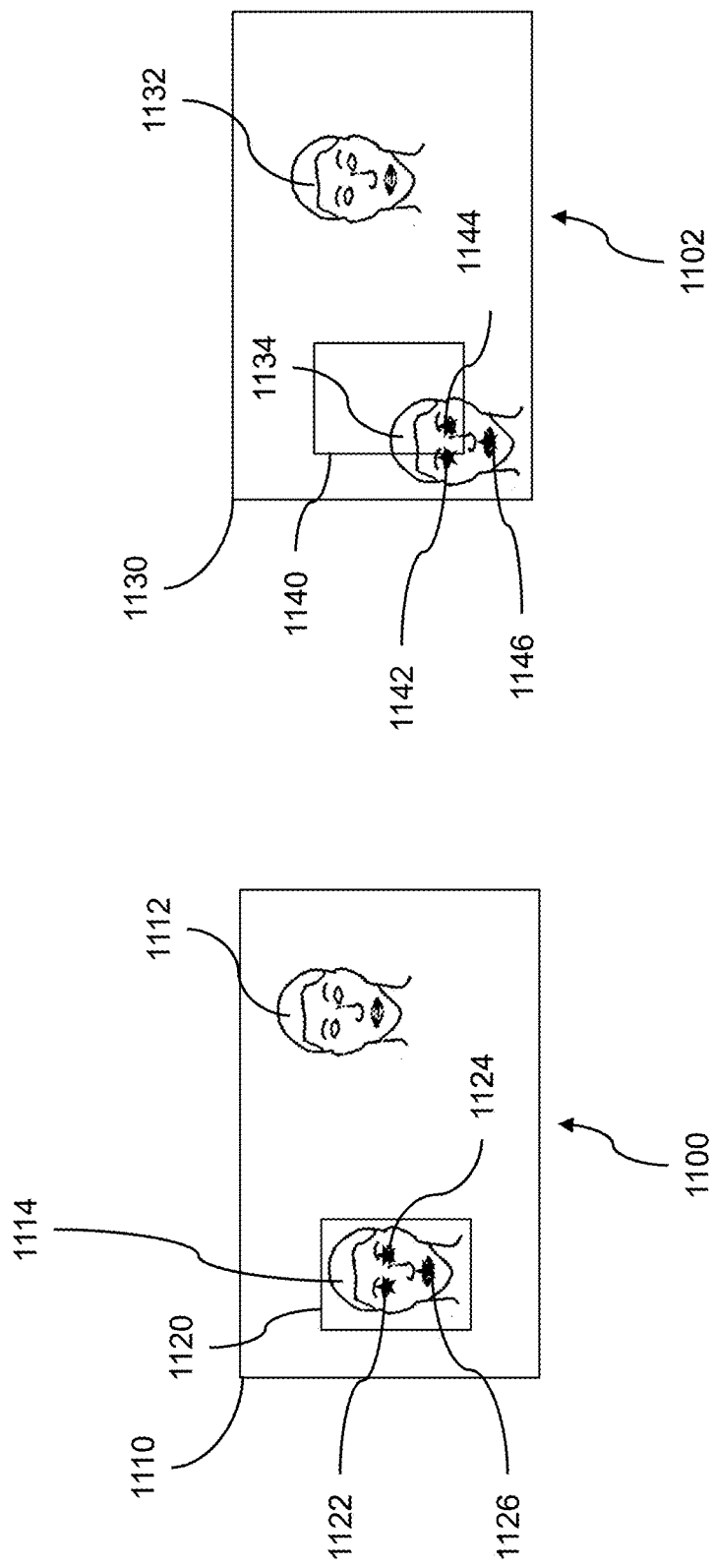
FIG. 11 illustrates feature extraction for multiple faces.

FIG. 11 illustrates feature extraction for multiple faces. Video data, audio data, and other data such as physiological data, can be obtained from an individual. The video data, audio data, and other data can be used for mental state analysis. The mental state analysis can use blink rate within vehicles to infer one or more mental states. Vehicles can include cameras and microphones, where the cameras and microphones can be used for collecting video including facial data, audio including voice data, etc. The video can be analyzed to detect a blink event based on a classifier, and blink-rate information can be determined using the blink event and one or more other blink events. The blink-rate information can be compensated for a context. Mental states of the individual can be inferred for the blink event, where the mental states are based on the blink event, the blink duration, and the compensated blink-rate information.

The feature extraction for multiple faces can be performed for faces that can be detected in multiple images. In embodiments, the features of multiple faces are extracted for evaluating mental states. Features of a face or a plurality of faces can be extracted from collected video data. The feature extraction can be performed by analysis, using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or existing observation, sample, datum, etc. should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When a new observation is received, then the classifier can be used to categorize the new observation. Classifiers can be used for many analysis applications, including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables involving various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in a single or in multiple frames of one or more videos.

Returning to FIG. 11, the detection of the first face, the second face, and multiple faces can include identifying facial landmarks, generating a bounding box, and prediction of a bounding box and landmarks for a next frame, where the next frame can be one of a plurality of frames of a video containing faces. A first video frame 1100 includes a frame boundary 1110, a first face 1112, and a second face 1114. The video frame 1100 also includes a bounding box 1120. Facial landmarks can be generated for the first face 1112. Face detection can be performed to initialize a second set of locations for a second set of facial landmarks for a second face within the video. Facial landmarks in the video frame 1100 can include the facial landmarks 1122, 1124, and 1126. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. The estimating of a second rough bounding box can include the bounding box 1120. Bounding boxes can also be estimated for one or more other faces within the boundary 1110. The bounding box can be refined, as can one or more facial landmarks. The refining of the second set of locations for the second set of facial landmarks can be based on localized information around the second set of facial landmarks. The bounding box 1120 and the facial landmarks 1122, 1124, and 1126 can be used to estimate future locations for the second set of locations for the second set of facial landmarks in a future video frame from the first video frame.

A second video frame 1102 is also shown. The second video frame 1102 includes a frame boundary 1130, a first face 1132, and a second face 1134. The second video frame 1102 also includes a bounding box 1140 and the facial landmarks, or points, 1142, 1144, and 1146. In other embodiments, multiple facial landmarks are generated and used for facial tracking of the two or more faces of a video frame, such as the shown second video frame 1102. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either the first face, the second face, or both faces, and so on. Other facial points can correspond to the second face. As mentioned above, multiple facial points can be determined within a frame. One or more of the other facial points that are determined can correspond to a third face. The location of the bounding box 1140 can be estimated, where the estimating can be based on the location of the generated bounding box 1120 shown in the first video frame 1100. The three facial points shown, facial points, or landmarks, 1142, 1144, and 1146, might lie within the bounding box 1140 or might not lie partially or completely within the bounding box 1140. For instance, the second face 1134 might have moved between the first video frame 1100 and the second video frame 1102. Based on the accuracy of the estimating of the bounding box 1140, a new estimation can be determined for a third, future frame from the video, and so on. The evaluation can be performed, all or in part, using semiconductor based logic.

Figure 12:
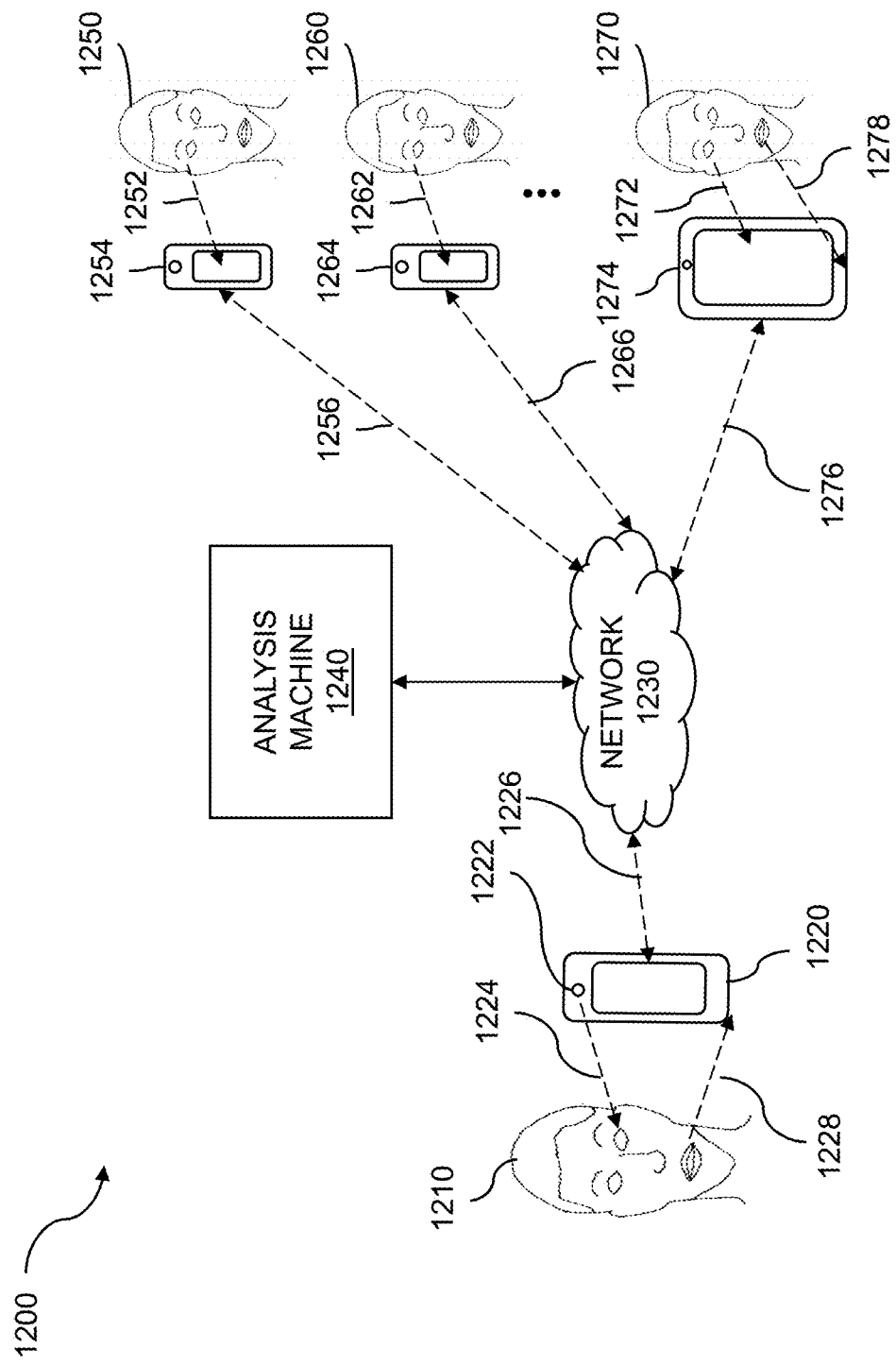
FIG. 12 shows live streaming for social video and social audio.

FIG. 12 shows an example of live streaming of social video and audio. The streaming of social video and social audio can be applied mental state analysis using blink rate within vehicles. Video of an individual within a vehicle can be obtained with an image capture device. The video can be analyzed to detect a blink event based on a classifier for a blink that was determined. A blink duration is evaluated of the individual for the blink event, and blink-rate information is determined using the blink event and one or more other blink events. The blink-rate information is compensated for a context, and mental states of the individual are inferred for the blink event. The mental states are based on the blink event, the blink duration of the individual, and the blink-rate information that was compensated. The live streaming and mental state analysis can be facilitated by a video capture device, a local server, a remote server, a semiconductor-based logic, and so on. The streaming can be live streaming and can include mental state analysis, mental state event signature analysis, etc. Live streaming video is an example of one-to-many social media, where video can be sent over the Network from one person to a plurality of people using a social media app and/or platform. Live streaming is one of numerous popular techniques used by people who want to disseminate ideas, send information, provide entertainment, share experiences, and so on. Some of the live streams, such as webcasts, online classes, sporting events, news, computer gaming, or video conferences can be scheduled, while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 1200 shows a user 1210 broadcasting a video live stream and an audio live stream to one or more people as shown by a first person 1250, a second person 1260, and a third person 1270. A portable, network-enabled, electronic device 1220 can be coupled to a front-facing camera 1222. The portable electronic device 1220 can be a smartphone, a PDA, a tablet, a laptop computer, and so on. The camera 1222 coupled to the device 1220 can have a line-of-sight view 1224 to the user 1210 and can capture video of the user 1210. The portable electronic device 1220 can be coupled to a microphone (not shown). The microphone can capture voice data 1228 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 1240 using a network link 1226 to the Network 1230. The network link can be a wireless link, a wired link, and so on. The recommendation engine 1240 can recommend to the user 1210 an app and/or platform that can be supported by the server and can be used to provide a video live stream, an audio live stream, or both a video live stream and an audio live stream to one or more followers of the user 1210.

In the example 1200, the user 1210 has three followers: a first person 1250, a second person 1260, and a third person 1270. Each follower has a line-of-sight view to a video screen on a portable, networked electronic device. In other embodiments, one or more followers follow the user 1210 using any other networked electronic device, including a computer. In the example 1200, a first person 1250 has a line-of-sight view 1252 to the video screen of a device 1254; a second person 1260 has a line-of-sight view 1262 to the video screen of a device 1264, and a third person 1270 has a line-of-sight view 1272 to the video screen of a device 1274. The device 1274 can also capture audio data 1278 from the third person 1270. The portable electronic devices 1254, 1264, and 1274 can each be a smartphone, a PDA, a tablet, and so on. Each portable device can receive the video stream and the audio stream being broadcast by the user 1210 through the Network 1230 using the app and/or platform that can be recommended by the recommendation engine 1240. The device 1254 can receive a video stream and the audio stream using the network link 1256, the device 1264 can receive a video stream and the audio stream using the network link 1266, the device 1274 can receive a video stream and the audio stream using the network link 1276, and so on. The network link can be a wireless link, a wired link, a hybrid link, and so on. Depending on the app and/or platform that can be recommended by the recommendation engine 1240, one or more followers, such as the followers shown 1250, 1260, and 1270, can reply to, comment on, or otherwise provide feedback to the user 1210 using their respective devices 1254, 1264, and 1274.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 13:
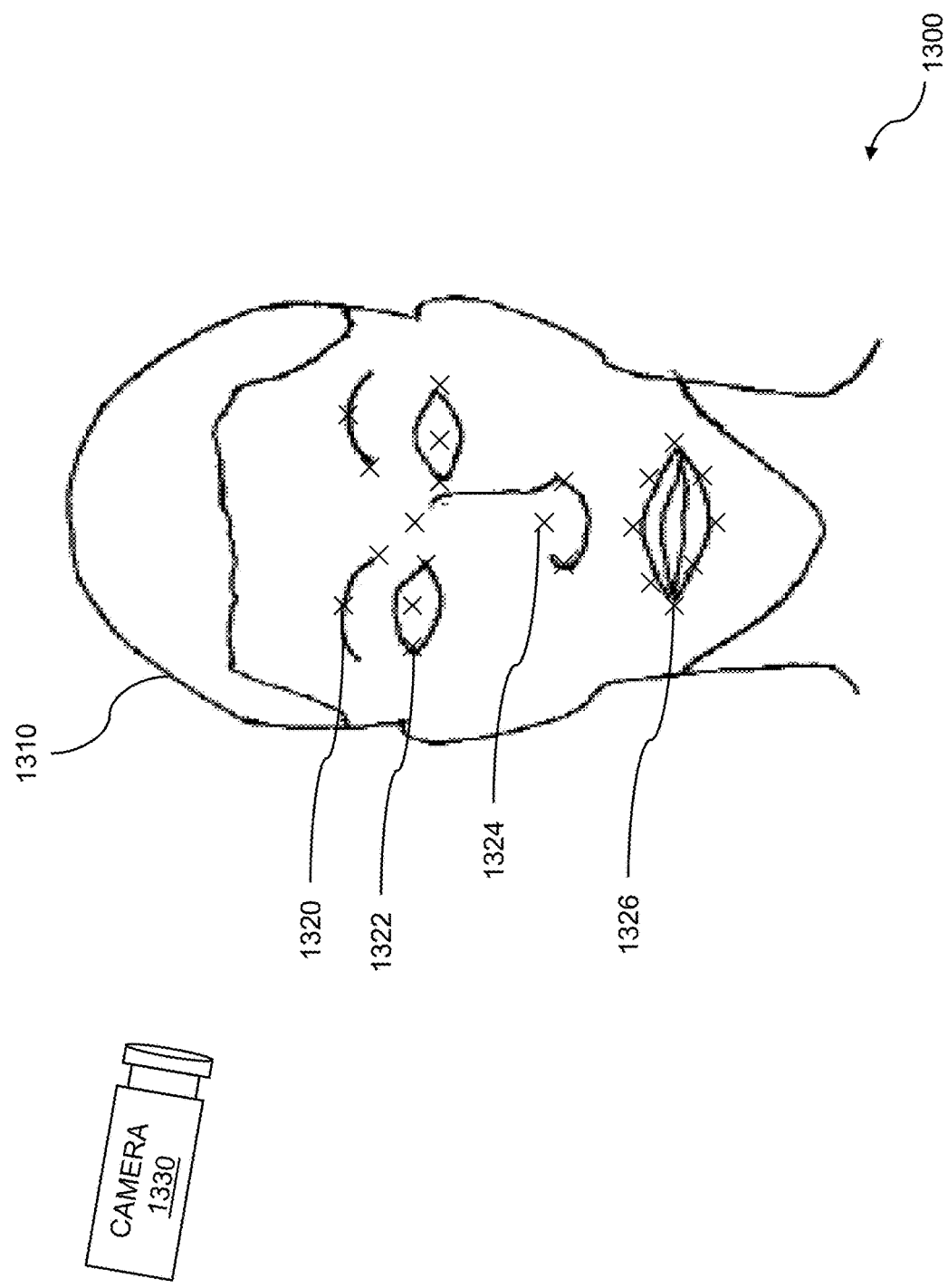
FIG. 13 illustrates example facial data collection including landmarks.

FIG. 13 shows example facial data collection including landmarks. Video data, audio data, and other data such as physiological data, can be collected from an individual for mental state analysis. The mental state analysis can use blink rate to infer one or more mental states. Vehicle artificial intelligence can be used for mental state analysis of individuals using blink rate within vehicles. Cameras and microphones within vehicles can be used for obtaining video and audio of an individual within a vehicle. The video is analyzed to detect a blink event. The blink event is evaluated for blink duration and blink-rate information is determined. The blink-rate information can be compensated for a context. Mental states of the individual are inferred for the blink event.

In the example 1300, facial data including facial landmarks can be collected using a variety of electronic hardware and software techniques. A face 1310 can be observed using a camera 1330 in order to collect facial data that includes facial landmarks. The facial data can be collected from a plurality of people using one or more of a variety of cameras. As previously discussed, the camera or cameras can include a webcam, where a webcam can refer to a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend on the position of the camera 1330 relative to the face 1310, the number of cameras used, the illumination of the face, etc. In some cases, if the face 1310 is poorly lit or over-exposed (e.g. in an area of bright light), the processing of the facial data to identify facial landmarks might be rendered more difficult. In another example, the camera 1330 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 1320, an outer eye edge 1322, a nose 1324, a corner of a mouth 1326, and so on. Multiple facial landmarks can be identified from the facial data that is captured. The facial landmarks that are identified can be analyzed to identify facial action units. The action units that can be identified can include AU02 outer brow raiser, AU14 dimpler, AU17 chin raiser, and so on. Multiple action units can be identified. The action units can be used alone and/or in combination to infer one or more mental states and emotions. A similar process can be applied to gesture analysis (e.g. hand gestures) with all of the analysis being accomplished or augmented by a mobile device, a server, semiconductor-based logic, and so on.

Figure 14:
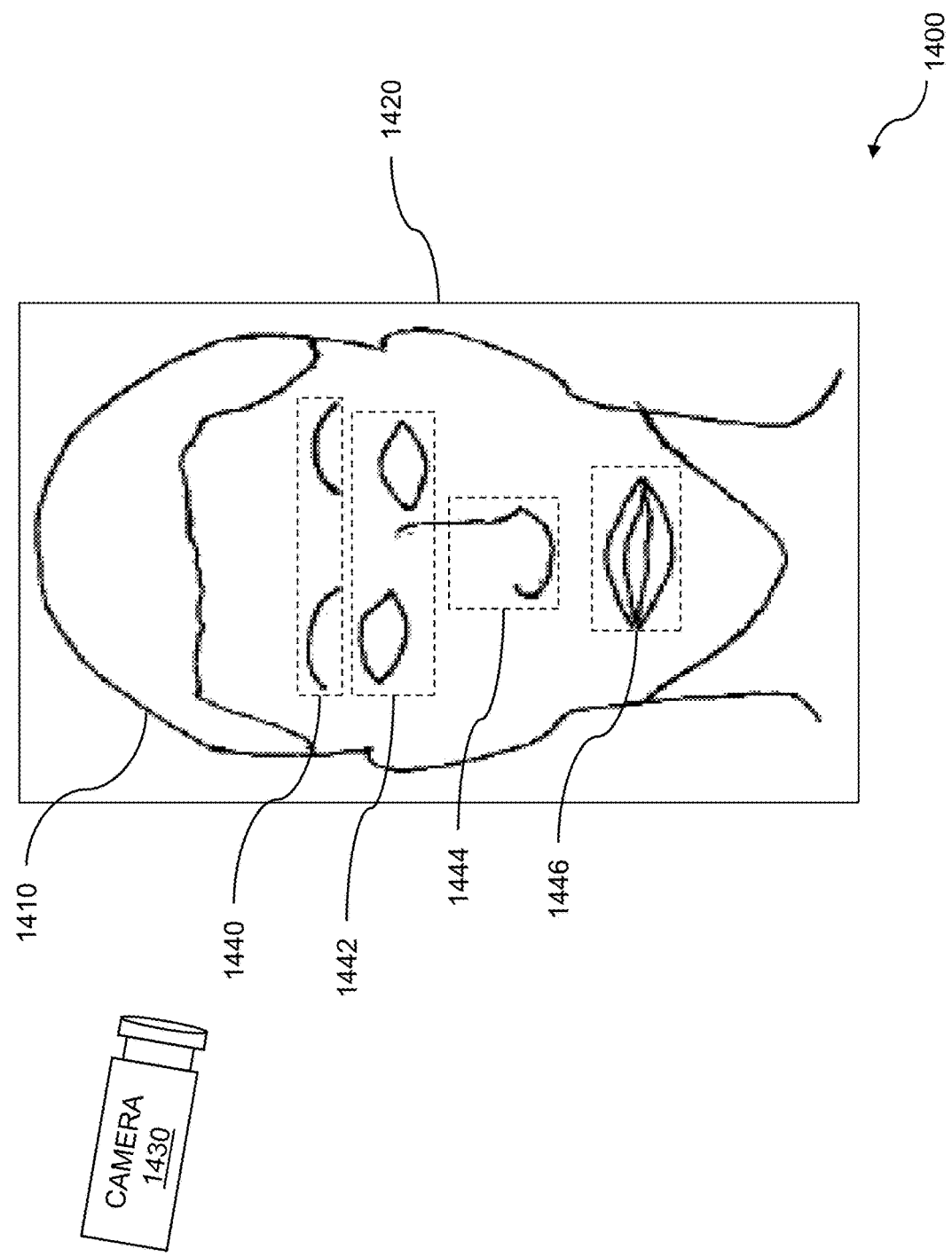
FIG. 14 shows example facial data collection including regions.

FIG. 14 shows example facial data collection including regions. Cameras, microphones, and other techniques can be used to collect video data, audio data, and other data such as physiological data from an individual. The video data, audio data, and other data can be analyzed to detect a blink event. The blink event can include a blink, a blink duration, blink rate, and so on. Mental state analysis can infer mental states by using the blink event, a blink duration, and blink-rate information that can be compensated for a context. Vehicle artificial intelligence can be used for evaluating of mental states. Video of an individual can be obtained within a vehicle with an image capture device. The video can be analyzed based on a classifier to determine a blink event. A blink duration can be evaluated and blink-rate information determined. The blink-rate information can be compensated for a context. Mental states of the individual can be inferred for the blink event, blink duration, and compensated blink-rate information.

Various regions of a face can be identified and used for a variety of purposes including facial recognition, facial analysis, and so on. Facial analysis can be used to determine, predict, estimate, etc. mental states, emotions, and so on of a person from whom facial data can be collected. The one or more emotions that can be determined by the analysis can be represented by an image, a figure, an icon, etc. The representative icon can include an emoji. One or more emoji can be used to represent a mental state, a mood, etc. of an individual, to represent food, a geographic location, weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1400, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1410 can be observed using a camera 1430, a sensor, a combination of cameras and/or sensors, and so on. The camera 1430 can be used to collect facial data that can be used to determine that a face is present in an image. When a face is present in an image, a bounding box 1420 can be placed around the face. Placement of the bounding box around the face can be based on detection of facial landmarks. The camera 1430 can be used to collect from the bounding box 1420 facial data, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1430 relative to the face 1410, the number of cameras and/or sensors used, the level of illumination of the face, any obstructions to viewing the face, and so on.

The facial regions that can be collected by the camera 1430, sensor, or combination of cameras and/or sensors can include any of a variety of facial features. The facial features that can be included in the facial regions that are collected can include eyebrows 1440, eyes 1442, a nose 1444, a mouth 1446, ears, hair, texture, tone, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include textures, gradients, colors, shapes, etc. The facial features can be used to determine demographic data, where the demographic data can include age, ethnicity, culture, gender, etc. Multiple textures, gradients, colors, shapes, and so on, can be detected by the camera 1430, sensor, or combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, wrinkles, and so on. Another texture that can be used to evaluate a facial region can include a smooth portion of skin such as a smooth portion of a check. A gradient in a facial region can include values assigned to local skin texture, shading, etc. A gradient can be used to encode, for example, a texture, by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, gender, etc. A shape in a facial region can include shape of a face, eyes, nose, mouth, ears, and so on. As with color in a facial region, shape in a facial region can be used to determine demographic data including ethnicity, culture, age, gender, and so on.

The facial regions can be detected based on detection of edges, boundaries, and so on, of features that can be included in an image. The detection can be based on various types of analysis of the image. The features that can be included in the image can include one or more faces. A boundary can refer to a contour in an image plane where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change, in color, brightness, etc. within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, edges, etc. Any classifier can be used for the analysis, including, but not limited to, density estimation, support vector machines (SVM), logistic regression, classification trees, and so on. By way of example, consider facial features that can include the eyebrows 1440. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique. The presence of an eyebrow furrow can indicate the person from whom the facial data can be collected is annoyed, confused, unhappy, and so on. In another example, consider facial features that can include a mouth 1446. One or more classifiers can be used to analyze the facial region that can include the mouth to determine a probability for either a presence or an absence of mouth edges turned up to form a smile. Multiple classifiers can be used to determine one or more facial expressions.

Figure 15:
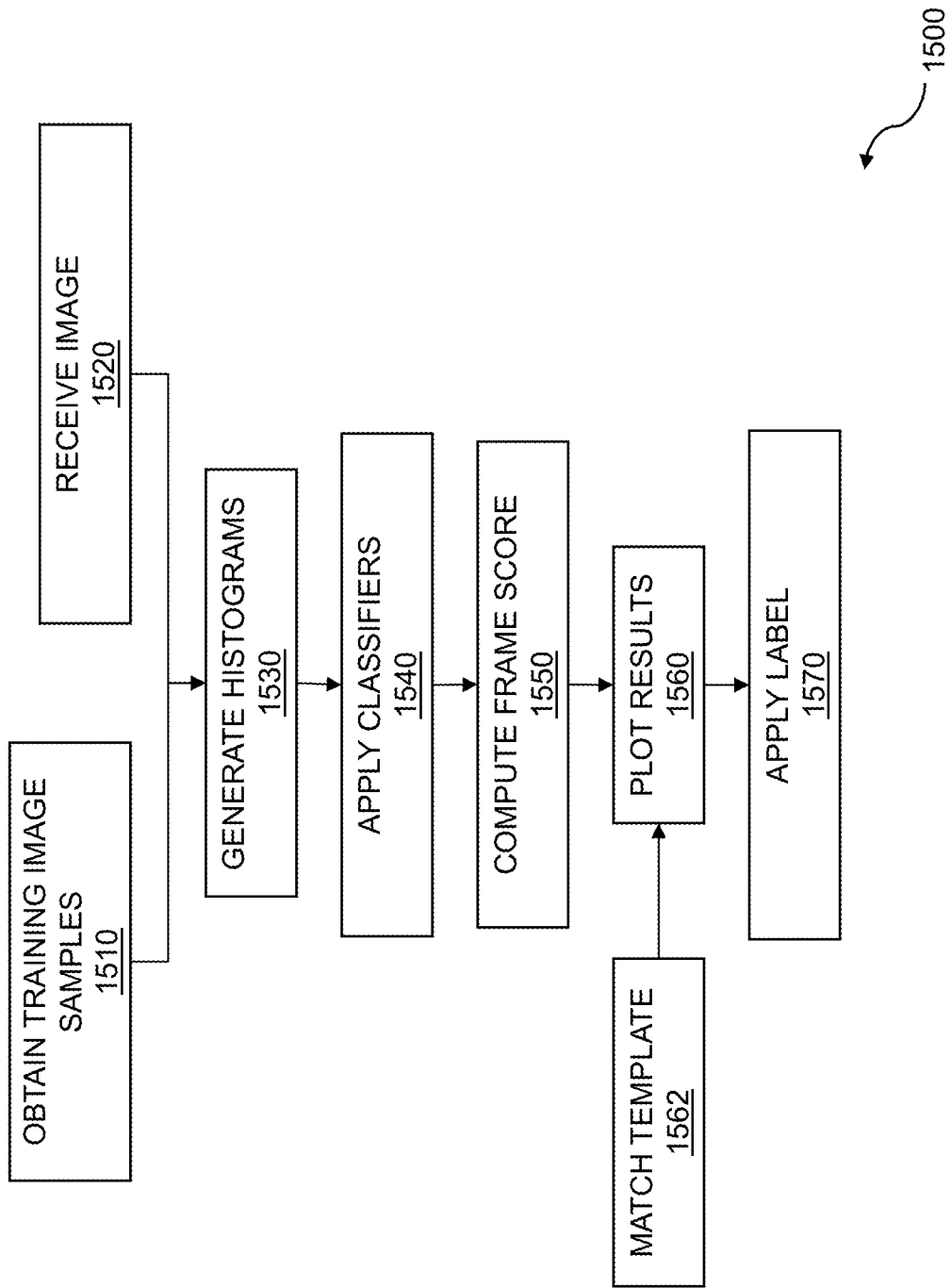
FIG. 15 is a flow diagram for detecting facial expressions.

FIG. 15 is a flow diagram for detecting facial expressions. Video data, audio data, and other data such as physiological data, can be collected from an individual within a vehicle. The video data, audio data, and other data can be used for mental state analysis. The mental state analysis can use a blink event, a blink duration, a blink rate, and blink-rate information that is compensated for a context to infer one or more mental states. Mental states of an individual can be inferred using vehicle artificial intelligence. The flow 1500, or portions thereof, can be implemented in semiconductor logic, can be accomplished using a mobile device, can be accomplished using a server device, and so on. The flow 1500 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1500 begins by obtaining training image samples 1510. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1500 continues with receiving an image 1520. The image 1520 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1500 continues with generating histograms 1530 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1500 continues with applying classifiers 1540 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1500 continues with computing a frame score 1550. The score computed for an image, where the image can be a frame from a video, can be used to determine the presence of a facial expression in the image or video frame. The score can be based on one or more versions of the image 1520 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1500 continues with plotting results 1560. The results that are plotted can include one or more scores for one or more frames computed over a given time t. For example, the plotted results can include classifier probability results from analysis of HoGs for a sequence of images and video frames. The plotted results can be matched with a template 1562. The template can be temporal and can be represented by a centered box function or another function. A best fit with one or more templates can be found by computing a minimum error. Other best-fit techniques can include polynomial curve fitting, geometric curve fitting, and so on. The flow 1500 continues with applying a label 1570. The label can be used to indicate that a particular facial expression has been detected in the one or more images or video frames which constitute the image that was received 1520. The label can be used to indicate that any of a range of facial expressions has been detected, including a smile, an asymmetric smile, a frown, and so on. Various steps in the flow 1500 may be changed in order, repeated, omitted, or the like without departing from the disclosed concepts. Various embodiments of the flow 1500 can be included in a computer program product embodied in a non-transitory computer readable medium that includes code executable by one or more processors. Various embodiments of the flow 1500, or portions thereof, can be included on a semiconductor chip and implemented in special purpose logic, programmable logic, and so on.

Figure 16:
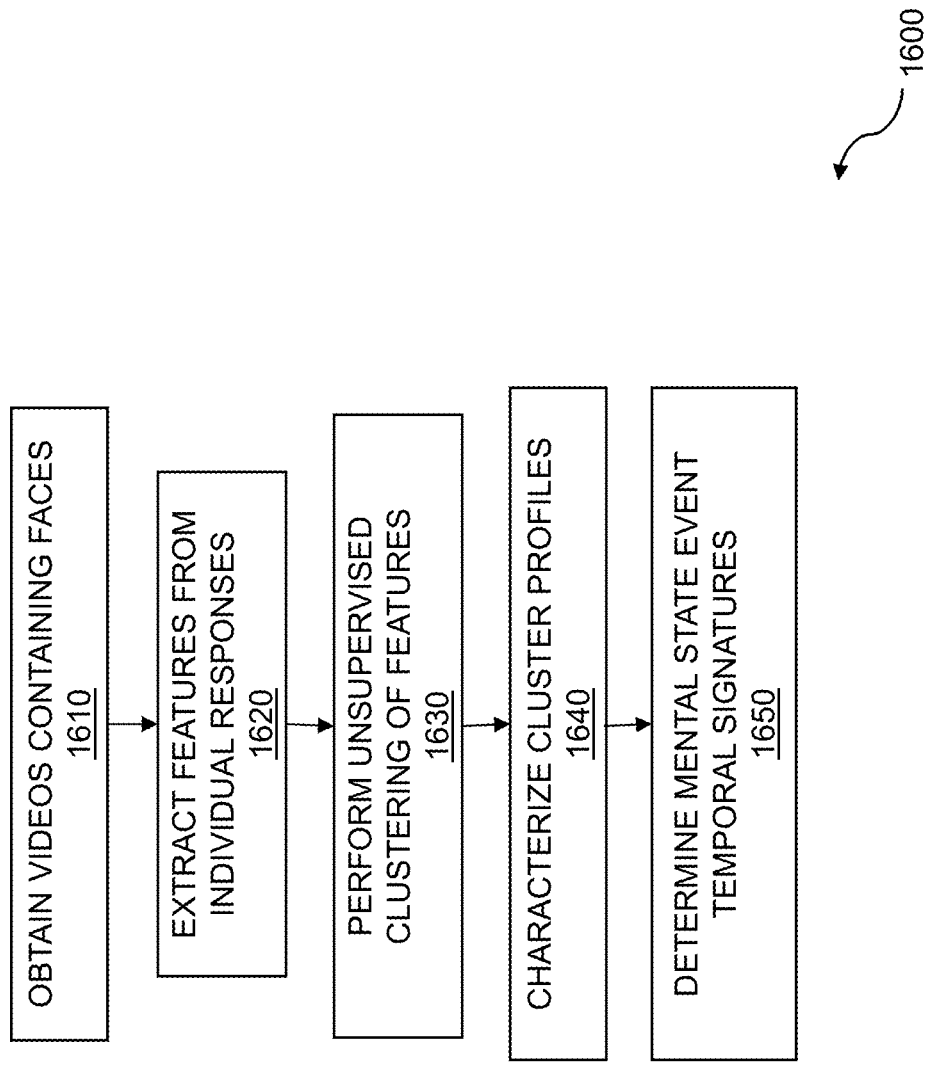
FIG. 16 is a flow diagram for large-scale clustering of facial events.

FIG. 16 is a flow diagram for the large-scale clustering of facial events. Video data and audio data collected from an individual can be analyzed to detect a blink event. Mental state analysis can infer mental states by using blink rate within a vehicle. The blink event can include a blink, a blink duration, blink rate, and so on. A vehicle with artificial intelligence can be used for evaluating mental states of a vehicle occupant. Video of an individual is obtained within a vehicle with an image capture device. Processors are used to analyze the video to detect a blink event based on a classifier for a blink that was determined. The blink event is determined by identifying that eyes of the individual are closed for a frame in the video using temporal analysis. Processors are used to evaluate a blink duration of the individual for the blink event and to determine blink-rate information using the blink event and one or more other blink events. The blink-rate information is compensated for a context, and mental states of the individual are inferred for the blink event, where the mental states are based on the blink event, the blink duration, and the blink-rate information that was compensated.

The large-scale clustering of facial events can be performed for data collected from a remote computing device. The facial events can be collected from people as they interact with a vehicle. The clustering and evaluation of facial events can be augmented using a mobile device, a server, semiconductor based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1600 includes obtaining videos containing faces 1610. The videos can be obtained using one or more cameras, where the cameras can include a webcam coupled to one or more devices employed by the one or more people using the web-based framework. The flow 1600 continues with extracting features from the individual responses 1620. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1600 continues with performing unsupervised clustering of features 1630. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1600 includes characterizing cluster profiles 1640. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared to various demographic groups, where the groups can be formed based on geographic location, age, ethnicity, gender, and so on.

The flow 1600 can include determining mental state event temporal signatures 1650. The mental state event temporal signatures can include information on rise time to facial expression intensity, fall time from facial expression intensity, duration of a facial expression, and so on. In some embodiments, the mental state event temporal signatures are associated with certain demographics, ethnicities, cultures, etc. The mental state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1600 may be changed in order, repeated, omitted, or the like without departing from the disclosed concepts. Various embodiments of the flow 1600 can be included in a computer program product embodied in a non-transitory computer readable medium that includes code executable by one or more processors. Various embodiments of the flow 1600, or portions thereof, can be included on a semiconductor chip and implemented in special purpose logic, programmable logic, and so on.

Figure 17:
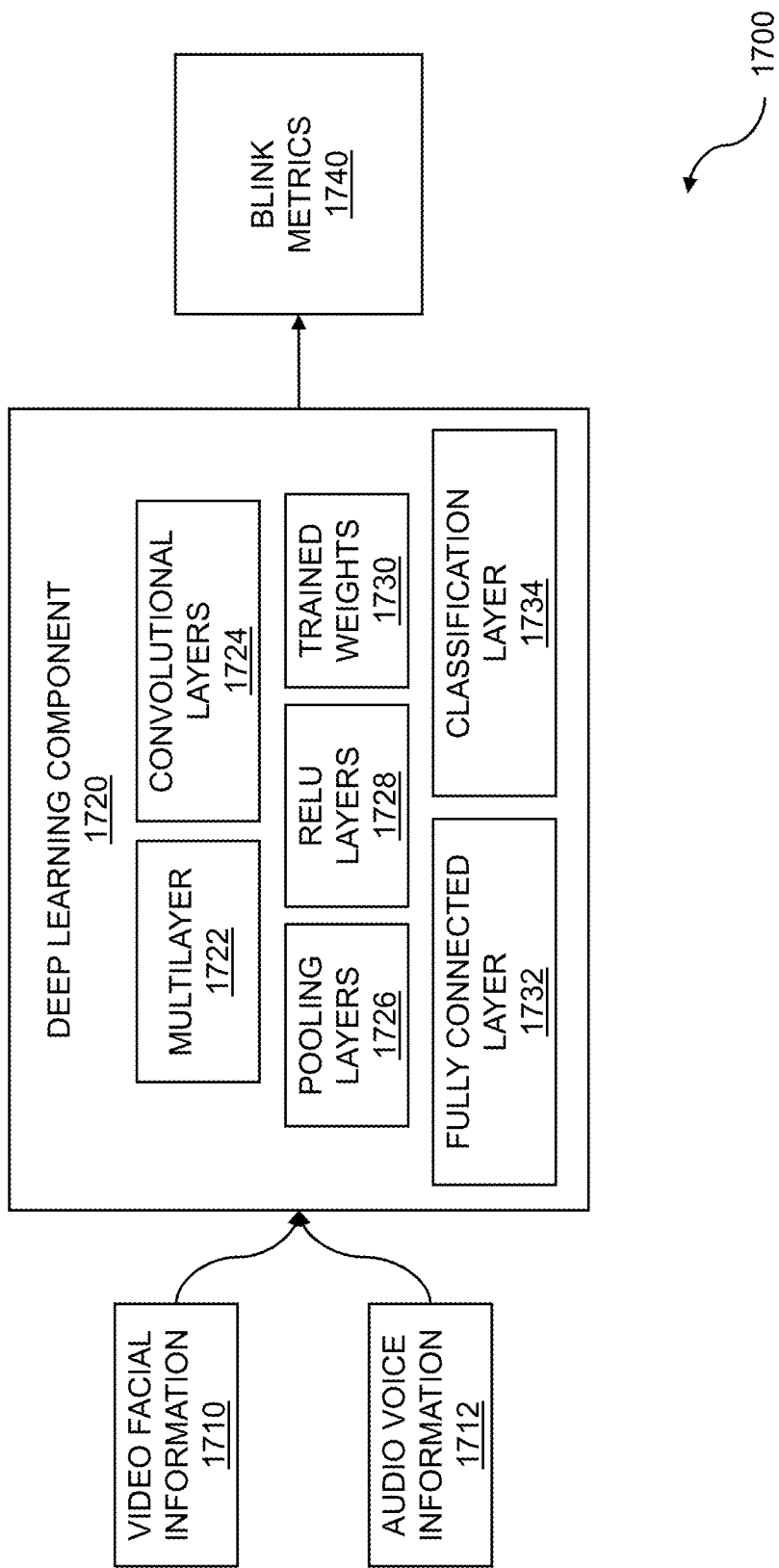
FIG. 17 shows a high-level diagram for deep learning for blink metrics.

FIG. 17 shows a high-level diagram for deep learning for blink metrics. Deep learning techniques such as convolutional neural networks can be applied to mental state analysis using blink rate of an operator or passenger in a vehicle. Video is obtained of an individual, where the individual can be an operator, passenger, or custodial driver in the vehicle, multiple vehicle occupants, etc. The video is analyzed to detect a blink event based on a classifier. A blink duration of the individual is evaluated for the blink event, and blink-rate information is determined using the blink event and one or more other blink events. The blink-rate information is compensated for a context, and mental states of the individual are inferred for the blink event. The mental states are based on the blink event, the blink duration of the individual, and the blink-rate information that was compensated. The mental states that are inferred can include one or more mental states of frustration, confusion, disappointment, hesitation, cognitive overload, focusing, engagement, exploration, confidence, trust, delight, disgust, skepticism, doubt, satisfaction, excitement, laughter, calmness, stress, anger, happiness, and curiosity.

A high-level diagram 1700 for deep learning is shown. The deep learning system can include a deep learning component 1720, where the deep learning component can include an artificial neural network (ANN). In embodiments, the artificial neural network can include a convolutional neural network (CNN). As discussed below, the CNN can include a variety of hardware and/or software components, where the hardware components and the software components can perform one or more techniques related to the CNN. The deep learning component can receive as input data that can be collected from a vehicle operator, a vehicle occupant, multiple individuals, and so on. The data provided to the deep learning component can include video facial information 1710. The video facial information can be collected using a camera, multiple cameras, or other video capture technique. In embodiments, the camera or cameras can include a webcam, a mobile camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The data provided to the deep learning component can include audio voice information 1712. The audio voice information can be collected using a microphone, a transducer, or other audio capture technique that can allow captured audio data to be used in the electronic system. In embodiments, the microphone, transducer, or other audio capture apparatus can be mounted in a vehicle, coupled to an electronic device such as a smartphone, personal digital assistant (PDA), a web microphone, and so on.

Returning to the deep learning component 1720, the deep learning component can include hardware components, software components, hybrid components that include both hardware and software, and so on. The hardware components and the software components can be related to a convolutional neural network (CNN) and can include algorithms, heuristics, code segments, integrated circuits or chips, processors, etc. The CNN can include multilayer 1722, there the multilayer can include one or more layers of an artificial neural network. The multilayer of the CNN can be used to classify the video facial information 1710, the audio voice information 1712, other information such as physiological information (not shown), etc. The multilayer can include an input layer, hidden layers, and output layer, and so on. The deep learning component can include convolutional layers 1724. The convolutional layers can perform convolution operations on input values, and can pass convolved results as outputs to the inputs a subsequent layer among the multiple layers of the CNN. The deep learning component can include pooling layers 1726. The pooling layers can be used to combine multiple outputs into a single output. The combining of the multiple outputs into a single output can be used for data compression, edge detection in a video image, voice detection in an audio clip, and so on.

The deep learning component 1720 can include rectified linear unit ReLU layers 1728. A ReLU layer can act as an activation function, where the activation function can define an output for a node based on an input to the node. The activation function can be nonlinear. The ReLU can include a ramp function, where the ramp function can "rectify" the input to the node to provide a rectified output. The rectifying of the input can include providing to the output the input value if the input value is greater than zero, or else zero. That is, $f(x)=\max(0, x)$. The deep learning component can include trained weights 1730. The weights can be used to adjust or "tune" the convolutional layers 1724. The weights can be adjusted by feeding forward weights into the convolutional layers. The weights can be adjusted by back propagation of adjusted weights. The back propagation of weights can include machine learning. The deep learning component can include a fully connected layer 1732. A fully connected layer can include receiving all outputs from a previous layer, and can include sending to all inputs in a next layer. The deep learning component can include a classification layer 1734. The classification layer can include applying one or more classifiers to outputs from a given layer. The one or more classifiers can be applied to the outputs from a fully connected layer. The results of applying classifiers can be blink metrics 1740. Blink metrics can include one or more of a blink event, blink duration, average blink duration, blink rate, blink rate context, and so on.

Figure 18:
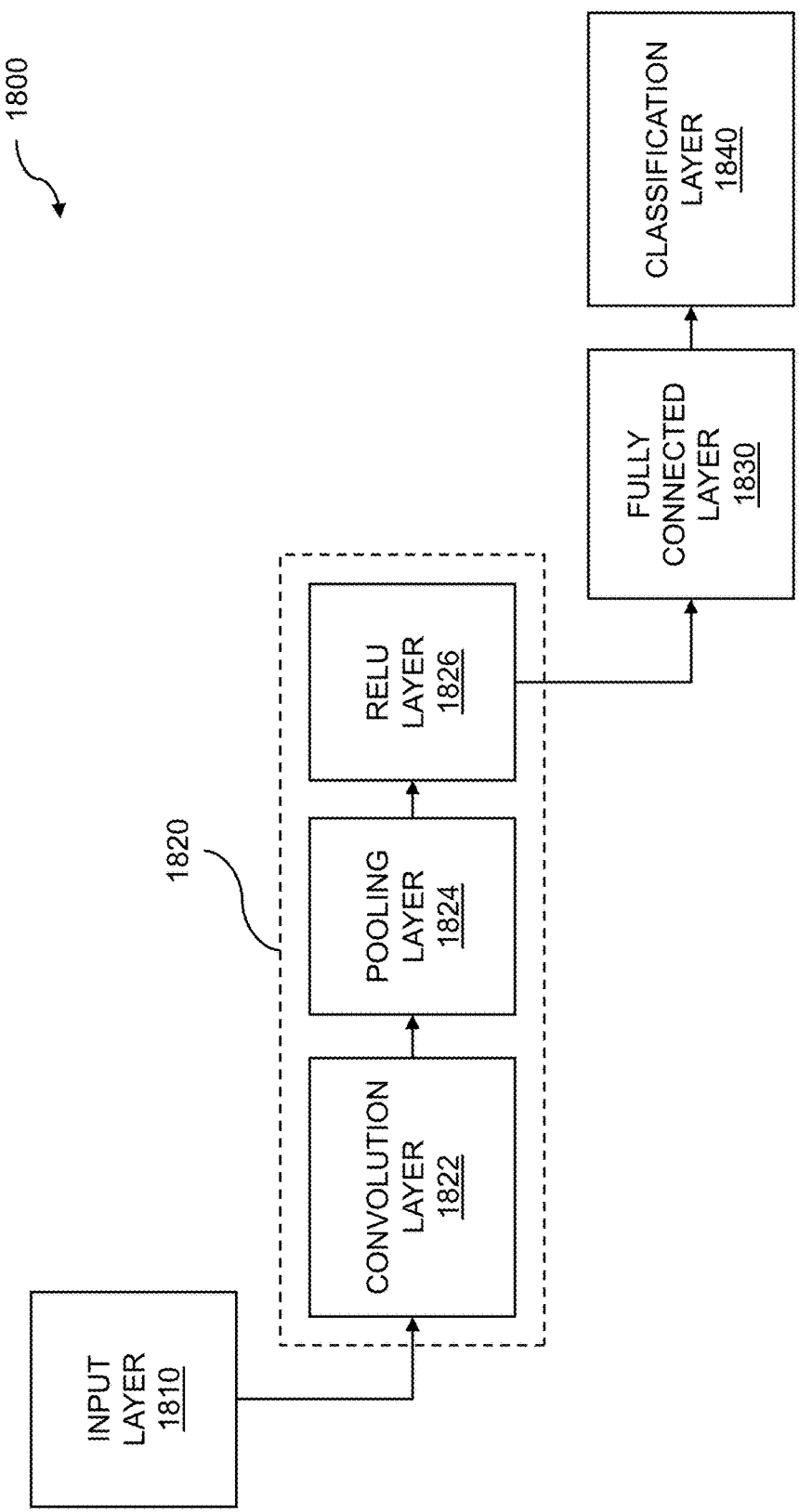
FIG. 18 illustrates a system diagram for deep learning for emotion analysis.

FIG. 18 illustrates a system diagram for deep learning for emotion analysis. Emotion analysis is a very complex task. Understanding and evaluating moods, emotions, or mental states requires a nuanced evaluation of facial expressions or other cues generated by people. Mental state analysis is important in many areas such as research, psychology, business, intelligence, law enforcement, and so on. The understanding of mental states can be used in a variety of fields, such as improving marketing analysis, assessing the effectiveness of customer service interactions and retail experiences, evaluating the consumption of content such as movies and videos, and aiding in the manipulation of a vehicle. Identifying points of frustration in a customer transaction can allow a company to act to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the mental state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the mental state of the audience can be obtained.

Analysis of facial expressions is also a complex undertaking. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be obtained, where the physiological data can be obtained using a camera or other image capture device, without contacting the person or persons. Respiration, heart rate, heart rate variability, perspiration, temperature, and other physiological indicators of mental state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more moods, mental states, emotional states, etc.

The artificial neural network which forms the basis for deep learning is based on layers. The layers can include an input layer, a convolution layer, a fully connected layer, a classification layer, and so on. The input layer can receive input data such as image data, where the image data can include a variety of formats including pixel formats. The input layer can then perform processing such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of mental state. The last layer of the convolutional neural network can be the final classification layer. The output of the final classification layer can be indicative of the mental states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be feed to next layer. Weights adjust the output of one layer as it is feed to the next layer. When the final layer is reached, the output of the final layer can be a facial expression, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward, from the input nodes, through the hidden nodes and on to the output nodes. Additionally, the weights can be updated during a backpropagation process through the multilayered analysis engine.

Returning to the figure, FIG. 18 illustrates a system diagram 1800 for deep learning. The system for deep learning can be accomplished using a convolution neural network or other techniques. The deep learning can accomplish facial recognition and analysis tasks, mental state analysis, and so on. The network includes an input layer 1810. The input layer 1810 receives image data. The image data can be input in a variety of formats, such as JPEG, TIFF, BMP, and GIF. Compressed image formats can be decompressed into arrays of pixels, wherein each pixel can include an RGB tuple. The input layer 1810 can then perform processing such as identifying boundaries of the face, identifying landmarks of the face, extracting features of the face, and/or rotating a face within the plurality of images.

The network includes a collection of intermediate layers 1820. The multilayered analysis engine can include a convolutional neural network. Thus, the intermediate layers can include a convolution layer 1822. The convolution layer 1822 can include multiple sublayers, including hidden layers within it. The output of the convolution layer 1822 feeds into a pooling layer 1824. The pooling layer 1824 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 1824. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1826. The output of the pooling layer 1824 can be input to the RELU layer 1826. In embodiments, the RELU layer implements an activation function such as $f(x)-\max(0,x)$, thus providing an activation with a threshold at zero. In some embodiments, the RELU layer 1826 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1822 and one or more hidden layers, and wherein the multilayered analysis engine can be used for emotional analysis.

The example 1800 includes a fully connected layer 1830. The fully connected layer 1830 processes each pixel/data point from the output of the collection of intermediate layers 1820. The fully connected layer 1830 takes all neurons in the previous layer and connects them to every single neuron it has. The output of the fully connected layer 1830 provides input to a classification layer 1840. The output of the classification layer 1840 provides a facial expression and/or mental state as its output. Thus, a multilayered analysis engine such as the one depicted in FIG. 18 processes image data using weights, models the way the human visual cortex performs object recognition and learning, and is effective for analysis of image data to infer facial expressions and mental states.

Figure 19:
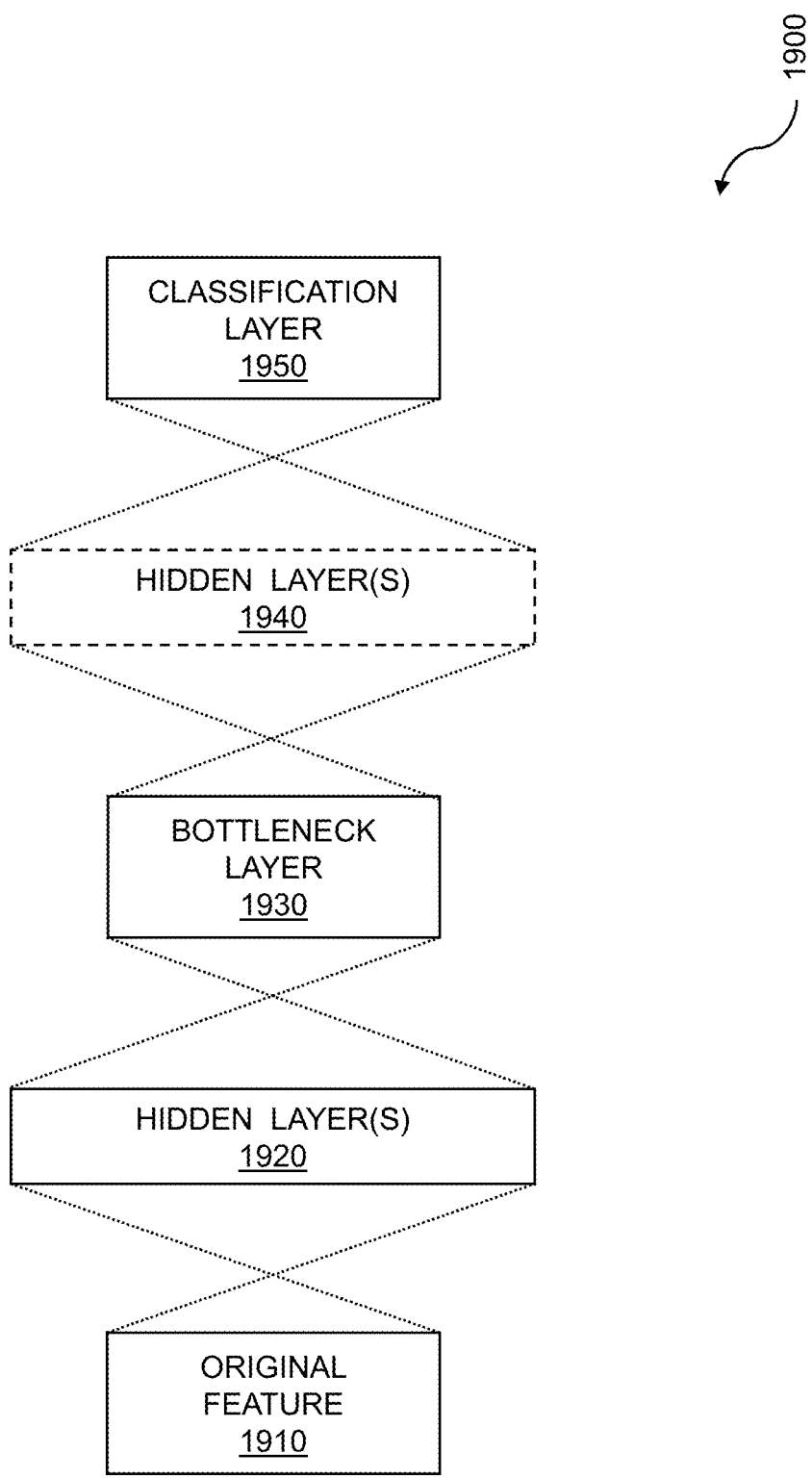
FIG. 19 shows a bottleneck layer within a deep learning environment

FIG. 19 shows a bottleneck layer within a deep learning environment. A plurality of layers in a deep neural network (DNN) can include a bottleneck layer. The bottleneck layer can be used for mental state analysis using blink rate within vehicles. A deep neural network can apply classifiers such as image classifiers, facial classifiers, blink classifiers, audio classifiers, speech classifiers, physiological classifiers, and so on. The classifiers can be learned by analyzing mental state data. Video is obtained of an individual within a vehicle with an image capture device. The video is analyzed to detect a blink event based on a classifier. The blink event is determined by identifying that eyes of the individual are closed for a frame in the video. The blink event is determined using temporal analysis. A blink duration of the individual is evaluated for the blink event. Blink-rate information is determined using the blink event and one or more other blink events, and the blink-rate information is compensated for a context. Mental states of the individual are inferred for the blink event, where the mental states are based on the blink event, the blink duration of the individual, and the blink-rate information that was compensated.

Layers of a deep neural network can include a bottleneck layer 1900. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1910. A feature such as an image feature can include points, edges, objects, boundaries between and among regions, properties, and so on. The deep neural network can include one or more hidden layers 1920. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1930. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 1940. The number of the hidden layers can include zero hidden layers, one hidden layer, a plurality of hidden layers, and so on. The hidden layers following the bottleneck layer can include more nodes than the bottleneck layer. The deep neural network can include a classification layer 1950. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 20:
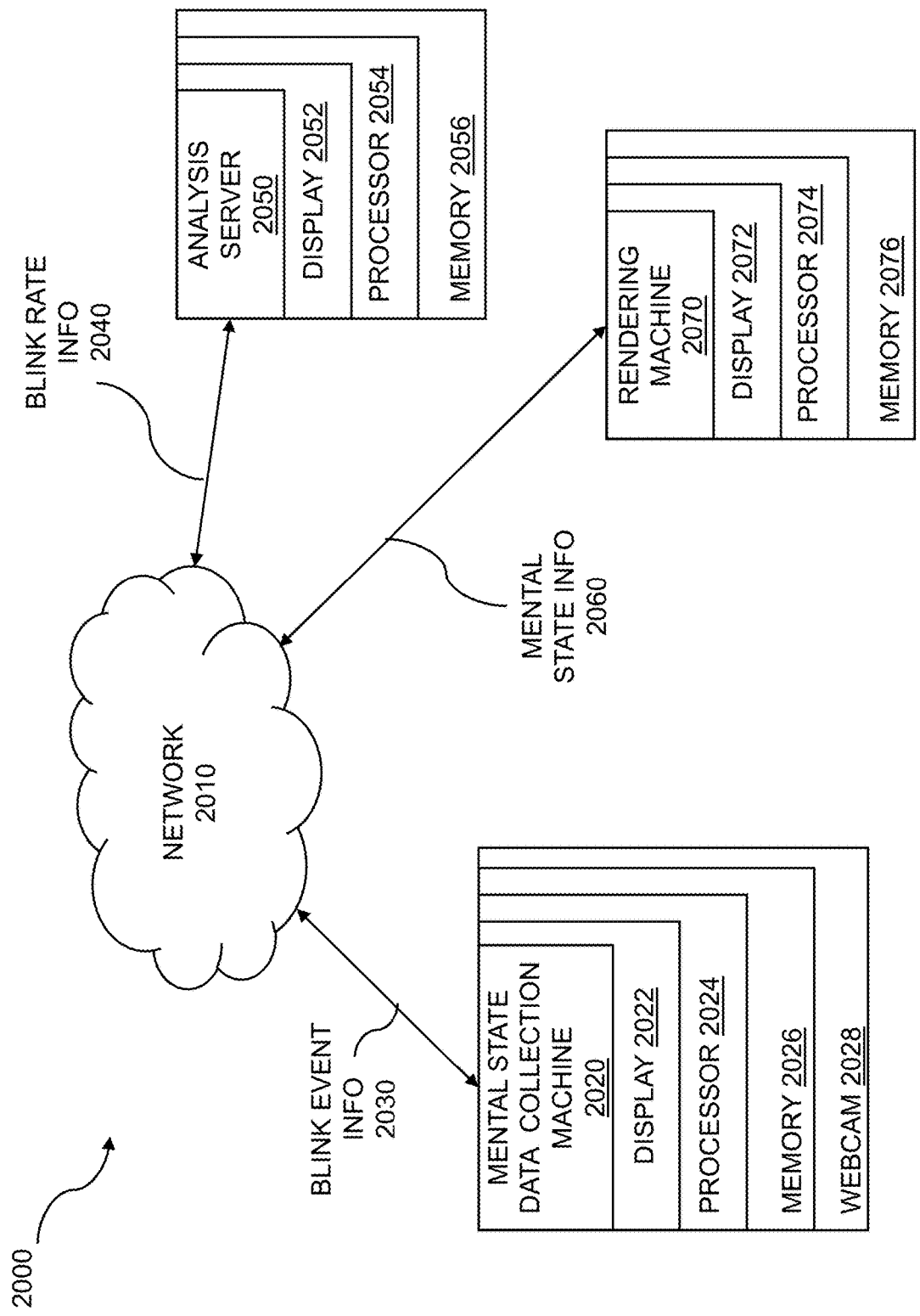
FIG. 20 is a system diagram for mental state analysis using blink-rate within vehicles.

FIG. 20 is a system diagram for mental state analysis using blink-rate within vehicles. The system 2000 can include one or more computers coupled together by a communication link or network 2010 such as the Network. The system 2000 can also include a mental state collection machine 2020, which can also be referred to as a client machine. The mental state collection machine 2020 includes a memory 2026 which stores instructions, one or more processors 2024 coupled to the memory, a display 2022, and a webcam 2028. The memory 2024 can be used for storing instructions, mental state data, blink-rate or blink event information, media presentations, and so on. The display 2022 can be any electronic display, including but not limited to, a computer display, a laptop screen, a net-book screen, a tablet screen, a cell phone display, a mobile device display, a remote with a display, a television, a projector, or the like. The webcam 2028, as the term is used herein, can refer to an in-vehicle camera, a camera on a computer (such as a laptop, a net-book, a tablet, or the like), a video camera, a still camera, a cell phone camera, a mobile device camera (including, but not limited to, a front-side camera), a thermal imager, a CCD device, a three-dimensional camera, a depth or plenoptic camera, multiple webcams used to capture different views of viewers, or any other type of image capture apparatus that allows image data to be captured and used by an electronic system.

An individual can interact with the mental state collection machine 2020, interact with another computer, or view a media presentation on another electronic display, among other activities. The mental state collection machine 2020 can capture video of the interacting individual, and analyze, using one or more processors, the video to detect a blink event based on a classifier for a blink that was determined. The blink event can be determined by identifying that eyes of the individual are closed for a frame in the video. Analyzing that the eyes of the individual are closed can include using temporal analysis The mental state collection machine 2020 can then infer mental states based on blink event information, the blink-rate information, or in some way process mental state data that was collected. The mental state collection machine 2020 can then send the blink event information 2030 of the blink-rate information to another computer (such as the analysis server 2050) across the network 2010 or using another computer-aided communications medium. In some embodiments, the mental state collection machine 2020 sends the raw video showing a blinking individual to another machine. In other embodiments, the mental state collection machine infers mental states and sends the mental states to another machine, such as the rendering machine 2070. In some embodiments, the one or more processors 2024 can be configured to perform a computer-implemented method for mental state analysis comprising: obtaining video of an individual within a vehicle with an image capture device; analyzing, using one or more processors, the video to detect a blink event based on a classifier for a blink that was determined wherein the blink event is determined by identifying that eyes of the individual are closed for a frame in the video using temporal analysis; evaluating, using the one or more processors, a blink duration of the individual for the blink event; determining, using the one or more processors, blink-rate information using the blink event and one or more other blink events; compensating, using the one or more processors, the blink-rate information for a context; inferring, using the one or more processors, mental states of the individual for the blink event, wherein the mental states are based on the blink event, the blink duration of the individual, and the blink-rate information that was compensated.

Some embodiments can include an analysis server 2050. The analysis server 2050 can include one or more processors 2054 coupled to a memory 2056 to store instructions. In embodiments, the analysis server 2050 includes a display 2052. The analysis server 2050 can receive the blink event information 2030 or blink rate information 2040 from the mental state collection machine 2020 through the network 2010. The one or more processors 2054 can be configured to perform a computer-implemented method for mental state analysis, which, in embodiments, comprises receiving eye blink-rate information obtained from video of an individual and inferring mental states of the individual based on the eye blink-rate information. In some embodiments, the analysis server 2050 is configured as a web server, so the inferring of the mental states can be performed by a web service.

The system 2000 can include a rendering machine 2070. The rendering machine can include one or more processors 2074 coupled to a memory 2076 to store instructions and a display 2072. The rendering machine 2070 can receive the mental state information 2060 from the network 2010 such as the Internet, or another computer-aided communication method. The mental state information 2060 can include eye blink-rate information from the analysis server 2050 or from the mental state data collection machine 2020, and can render an output to the display 2072. So, the system 2000 can enable a computer-implemented method for mental state analysis comprising receiving eye blink-rate information based on video of an individual, receiving mental state information inferred from the eye blink-rate information, and rendering one or more of the eye blink-rate information and the mental state information which was inferred.

The system 2000 can comprise a computer system for mental state analysis comprising: a memory which stores instructions; one or more processors attached to the memory wherein the one or more processors, when executing the instructions which are stored, are configured to: obtain video of an individual within a vehicle with an image capture device; analyze the video to detect a blink event based on a classifier for a blink that was determined wherein the blink event is determined by identifying that eyes of the individual are closed for a frame in the video using temporal analysis; evaluate a blink duration of the individual for the blink event; determine blink-rate information using the blink event and one or more other blink events; compensate the blink-rate information for a context; and infer mental states of the individual for the blink event, wherein the mental states are based on the blink event, the blink duration of the individual, and the blink-rate information that was compensated.

The system 2000 can comprise a computer program product embodied in a non-transitory computer readable medium for mental state analysis, the computer program product comprising code which causes one or more processors to perform operations of: obtaining video of an individual within a vehicle with an image capture device; analyzing, using one or more processors, the video to detect a blink event based on a classifier for a blink that was determined wherein the blink event is determined by identifying that eyes of the individual are closed for a frame in the video using temporal analysis; evaluating, using the one or more processors, a blink duration of the individual for the blink event; determining, using the one or more processors, blink-rate information using the blink event and one or more other blink events; compensating, using the one or more processors, the blink-rate information for a context; and inferring, using the one or more processors, mental states of the individual for the blink event, wherein the mental states are based on the blink event, the blink duration of the individual, and the blink-rate information that was compensated.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"— may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
    obtaining video of an individual within a vehicle with an image capture device;
    analyzing, using one or more processors, the video to detect a blink event based on a classifier for a blink that was determined wherein the blink event is determined by identifying that eyes of the individual are closed for a frame in the video using temporal analysis, and wherein the analyzing filters out looking down by the individual;
    evaluating, using the one or more processors, a blink duration of the individual for the blink event;
    determining, using the one or more processors, blink-rate information using the blink event and one or more other blink events;
    compensating, using the one or more processors, the blink-rate information for a context; and
    inferring, using the one or more processors, mental states of the individual for the blink event, wherein the mental states are based on the blink event, the blink duration of the individual, and the blink-rate information that was compensated.

2. The method of claim 1 wherein the individual is a passenger in the vehicle.

3. The method of claim 1 wherein the individual is a driver of the vehicle.

4. The method of claim 3 wherein the driver is a custodial driver.

5. The method of claim 1 further comprising manipulating the vehicle based on the mental states that were inferred.

6. The method of claim 5 wherein the manipulating the vehicle includes recommending action.

7. The method of claim 5 wherein the manipulating the vehicle includes initiating a locking out operation, recommending a break for an occupant, recommending a different route, recommending how far to drive, controlling the vehicle in response to traffic, adjusting seats, adjusting mirrors, adjusting climate control, adjusting lighting, adjusting music, generating audio stimuli, activating a braking system, or activating steering control.

8. The method of claim 5 wherein the manipulating the vehicle includes recommending content to the individual.

9. The method of claim 1 wherein the image capture device includes a near-infrared image capture device.

10. The method of claim 9 wherein the video includes near-infrared video.

11. The method of claim 1 wherein the mental states that were inferred indicate one or more of attention, concentration, boredom, fatigue, or cognitive load for the individual.

12. The method of claim 1 wherein the mental states that were inferred indicate drowsiness for the individual.

13. The method of claim 1 further comprising locating a portion of a face with eyes.

14. The method of claim 13 further comprising performing temporal analysis on the portion of the face.

15. The method of claim 1 further comprising determining a difference in blinking by the individual and typical blinking for the individual.

16. The method of claim 15 wherein the inferring mental states of the individual is further based on the difference in blinking by the individual and typical blinking for the individual.

17. The method of claim 1 further comprising evaluating average blink duration.

18. The method of claim 1 further comprising evaluating blinking for a group of people of which the individual is a part of the group.

19. The method of claim 18 further comprising determining a difference in blinking between the individual and a remainder of the group.

20. The method of claim 1 further comprising aggregating the blink-rate information for the individual with blink-rate information for a plurality of other people.

21. The method of claim 1 further comprising correlating the blink-rate information with activities performed by the individual.

22. The method of claim 1 wherein the blink-rate information is correlated to a stimulus that the individual is encountering.

23. The method of claim 1 wherein the video is obtained from multiple sources.

24. The method of claim 1 wherein the video is collected sporadically.

25. The method of claim 1 wherein the inferring includes evaluation of an impaired state.

26. The method of claim 1 wherein the mental states, which were inferred, are used to modify a media presentation.

27. A computer program product embodied in a non-transitory computer readable medium for mental state analysis, the computer program product comprising code which causes one or more processors to perform operations of:
   obtaining video of an individual within a vehicle with an image capture device;
   analyzing, using one or more processors, the video to detect a blink event based on a classifier for a blink that was determined wherein the blink event is determined by identifying that eyes of the individual are closed for a frame in the video using temporal analysis, and wherein the analyzing filters out looking down by the individual;
   evaluating, using the one or more processors, a blink duration of the individual for the blink event;
   determining, using the one or more processors, blink-rate information using the blink event and one or more other blink events;
   compensating, using the one or more processors, the blink-rate information for a context; and
   inferring, using the one or more processors, mental states of the individual for the blink event, wherein the mental states are based on the blink event, the blink duration of the individual, and the blink-rate information that was compensated.

28. A computer system for mental state analysis comprising:
   a memory which stores instructions;
   one or more processors attached to the memory wherein the one or more processors, when executing the instructions which are stored, are configured to:
      obtain video of an individual within a vehicle with an image capture device;
      analyze the video to detect a blink event based on a classifier for a blink that was determined wherein the blink event is determined by identifying that eyes of the individual are closed for a frame in the video using temporal analysis, wherein analyzing the video includes filtering out looking down by the individual;
      evaluate a blink duration of the individual for the blink event;
      determine blink-rate information using the blink event and one or more other blink events;
      compensate the blink-rate information for a context; and
      infer mental states of the individual for the blink event, wherein the mental states are based on the blink event, the blink duration of the individual, and the blink-rate information that was compensated.

* * * * *